(12) United States Patent
Shendure et al.

(10) Patent No.: US 9,809,904 B2
(45) Date of Patent: Nov. 7, 2017

(54) METHODS FOR RETRIEVAL OF SEQUENCE-VERIFIED DNA CONSTRUCTS

(75) Inventors: Jay Shendure, Seattle, WA (US); Jerrod Schwartz, Seattle, WA (US); Jacob Kitzman, Seattle, WA (US); Rupali Patwardhan, Seattle, WA (US); Joseph Hiatt, Seattle, WA (US)

(73) Assignee: UNIVERSITY OF WASHINGTON THROUGH ITS CENTER FOR COMMERCIALIZATION, Seattle, WA (US)

( * ) Notice: Subject to any disclaimer, the term of this patent is extended or adjusted under 35 U.S.C. 154(b) by 0 days.

(21) Appl. No.: 13/453,947

(22) Filed: Apr. 23, 2012

(65) Prior Publication Data

US 2012/0283110 A1 Nov. 8, 2012

Related U.S. Application Data

(60) Provisional application No. 61/478,016, filed on Apr. 21, 2011.

(51) Int. Cl.
*C40B 20/04* (2006.01)
*C12Q 1/68* (2006.01)

(52) U.S. Cl.
CPC ............ *C40B 20/04* (2013.01); *C12Q 1/6806* (2013.01); *C12Q 1/6853* (2013.01)

(58) Field of Classification Search
CPC ......... C40B 20/04; C40B 50/14; C40B 50/16; C12N 15/01; C12N 15/10; C12N 15/1031; C12Q 1/6809; C12Q 1/6844; C12Q 1/6853; C12Q 1/6855; C12Q 1/686
See application file for complete search history.

(56) References Cited

U.S. PATENT DOCUMENTS

| | | | |
|---|---|---|---|
| 6,432,360 B1 * | 8/2002 | Church | B01J 19/0046 422/50 |
| 2010/0015668 A1 * | 1/2010 | Staehler et al. | 435/91.2 |
| 2013/0224729 A1 * | 8/2013 | Church | C12Q 1/6853 435/5 |

OTHER PUBLICATIONS

Tucker T., et al. 2009 American Journal of Human Genetics 85: 142-154.*
Bang, D., Church, G. M. Gene synthesis by circular assembly amplification. *Nature* 2008; 5:37-39.
Binkowski, B. F., Richmond, K. E., et al. Correcting errors in synthetic DNA through consensus shuffling. *Nucleic Acids Research* 2005; 33:e55.
Borovkov, A. Y., Loskutov, A. V., et al. High-quality gene assembly directly from unpurified mixtures of microarray-synthesized oligonucleotides. *Nucleic Acids Research* 2010; 38:e180.
Carr, P. A., Park, J. S., et al. Protein-mediated error correction for *de novo* DNA synthesis. *Nucleic Acids Research* 2004; 32:e162.
Fuhrmann, M., Oertel, W., et al. Removal of mismatched bases from synthetic genes by enzymatic mismatch cleavage. *Nucleic Acids Research* 2005; 33:e58.
Gibson, D. G., Smith, H. O., et al. Chemical synthesis of the mouse mitochondrial genome. *Nature Methods* 2010; 7:901-905.
Gibson, D. G., Benders, G. A., et al. Complete Chemical Synthesis, Assembly, and Cloning of a *Mycoplasma genitalium* Genome. *Science* 2008; 319:1215-1220.
Gibson, D. G.,Glass, J. I, et al. Creation of a Bacterial Cell Controlled by a Chemically Synthesized Genome. *Science* 2010; 329:52-56.
Green, R. E., Krause, J., et al. A Draft Sequence of the Neandertal Genome. *Science* 2010; 328:710-722.
Hiatt, J. B., Patwardhan, R. P., et al. Parallel, tag-directed assembly of locally derived short sequence reads. *Nat Methods* 2010; 7:119-122.
Hoover, D. M., Lubkowski, J. DNAWorks: an automated method for designing oligonucleotides for PCR-based gene synthesis. *Nucleic Acids Research* 2002; 30:e43.
Kosuri, S., Eroshenko, N., et al. A Scalable Gene Synthesis Platform Using High-Fidelity DNA Microchips. *Nat Biotechnol* 2010; 1295-1299.
Leproust, E. M., Peck, B. J., et al. Synthesis of high-quality libraries of long (150mer) oligonucleotides by a novel depurination controlled process. *Nucleic Acids Research* 2010; 38:2522-2540.
Matzas, M., Stähler, P. F., et al. High-fidelity gene synthesis by retrieval of sequence-verified DNA identified using high-throughput pyrosequencing. *Nature Biotechnology* 2010; 28:1291-1295.
Maurer, K., Cooper, J., et al. Electrochemically Generated Acid and Its Containment to 100 Micron Reaction Areas for the Production of DNA Microarrays. *PLoS ONE* 2006; 1:e34.
Smith, J., Modrich, P. Removal of polymerase-produced mutant sequences from PCR products. *Proc. Natl. Acad. Sci.* 1997; 94:6847-6850.
Tian, J., Gong, H., et al. Accurate multiplex gene synthesis from programmable DNA microchips. *Nature* 2004; 432:1050-1054.

* cited by examiner

*Primary Examiner* — Christopher M Gross
(74) *Attorney, Agent, or Firm* — Perkins Coie LLP; Lara J. Dueppen

(57) ABSTRACT

In some embodiments, methods of recovering a sequence-verified target nucleic acid are provided. In some embodiments, such methods may include tagging each member of a nucleic acid library with a set of adaptor sequences; sequencing the tagged members of the nucleic acid library; and recovering the sequence-verified target nucleic acid from the tagged and sequenced members of the nucleic acid library using a dial-out selection method. In certain embodiments, the members of the nucleic acid library may be tagged with a second set of adaptor sequences.

16 Claims, 9 Drawing Sheets

SEQUENCE LISTING

<160> NUMBER OF SEQ ID NOS: 56

<210> SEQ ID NO 1
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1
ttattcgccc atttccctgg         20

<210> SEQ ID NO 2

```
<211> LENGTH: 20
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<223> OTHER INFORMATION: Phosphorylated 5' end

<400> SEQUENCE: 2
tggtcgaatg gctgctgatc                                              20

<210> SEQ ID NO 3
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 3
gagaatggct gctctccatg                                              20

<210> SEQ ID NO 4
<211> LENGTH: 20
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<223> OTHER INFORMATION: Phosphorylated 5' end

<400> SEQUENCE: 4
tggtcgaatg gctgctgatc                                              20

<210> SEQ ID NO 5
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 5
ggtagggtaa agagacctgg                                              20

<210> SEQ ID NO 6
<211> LENGTH: 20
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<223> OTHER INFORMATION: Phosphorylated 5' end

<400> SEQUENCE: 6
tggtcgaatg gctgctgatc                                              20

<210> SEQ ID NO 7
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 7
ggatactggc ggagtgcatg                                              20
```

<210> SEQ ID NO 8
<211> LENGTH: 20
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<223> OTHER INFORMATION: Phosphorylated 5' end

<400> SEQUENCE: 8
tggtcgaatg gctgctgatc                                           20

<210> SEQ ID NO 9
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 9
atttgatgag ttgccccatg                                           20

<210> SEQ ID NO 10
<211> LENGTH: 20
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<223> OTHER INFORMATION: Phosphorylated 5' end

<400> SEQUENCE: 10
tggtcgaatg gctgctgatc                                           20

<210> SEQ ID NO 11
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 11
ccgttgctag gagtctgaat                                           20

<210> SEQ ID NO 12
<211> LENGTH: 20
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<223> OTHER INFORMATION: Phosphorylated 5' end

<400> SEQUENCE: 12
tggtcgaatg gctgctgatc                                           20

<210> SEQ ID NO 13
<211> LENGTH: 60
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (21)..(23)

<223> OTHER INFORMATION: n is a, c, g, or t
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (30)..(32)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: misc_feature
<222> LOCATION: (38)..(40)
<223> OTHER INFORMATION: n is a, c, g, or t

<400> SEQUENCE: 13
cgacagtaac tacacggcga nnnagnntgn nngnnacnnn ttattcgccc atttccctgg    60

<210> SEQ ID NO 14
<211> LENGTH: 60
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (21)..(23)
<223> OTHER INFORMATION: n is a, c, g, or t
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (30)..(32)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: misc_feature
<222> LOCATION: (38)..(40)
<223> OTHER INFORMATION: n is a, c, g, or t

<400> SEQUENCE: 14
gtagcaattg gcaggtccat nnnttnngan nnanngtnnn gagaatggct gctctccatg    60

<210> SEQ ID NO 15
<211> LENGTH: 60
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (21)..(23)
<223> OTHER INFORMATION: n is a, c, g, or t
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (30)..(32)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: misc_feature

```
<222> LOCATION: (38)..(40)
<223> OTHER INFORMATION: n is a, c, g, or t

<400> SEQUENCE: 15
cgacagtaac tacacggcga nnnagnntgn nngnnacnnn ggtagggtaa agagacctgg      60

<210> SEQ ID NO 16
<211> LENGTH: 60
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (21)..(23)
<223> OTHER INFORMATION: n is a, c, g, or t
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (30)..(32)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: misc_feature
<222> LOCATION: (38)..(40)
<223> OTHER INFORMATION: n is a, c, g, or t

<400> SEQUENCE: 16
gtagcaattg gcaggtccat nnnttnngan nnanngtnnn ggatactggc ggagtgcatg      60

<210> SEQ ID NO 17
<211> LENGTH: 60
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (21)..(23)
<223> OTHER INFORMATION: n is a, c, g, or t
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (30)..(32)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: misc_feature
<222> LOCATION: (38)..(40)
<223> OTHER INFORMATION: n is a, c, g, or t

<400> SEQUENCE: 17
cgacagtaac tacacggcga nnnagnntgn nngnnacnnn atttgatgag ttgccccatg      60

<210> SEQ ID NO 18
<211> LENGTH: 60
<212> TYPE: DNA
<213> ORGANISM: Artificial Sequence
<220> FEATURE:
<223> OTHER INFORMATION: Synthetic oligonucleotide
<220> FEATURE:
```

```
<221> NAME/KEY: misc_feature
<222> LOCATION: (21)..(23)
<223> OTHER INFORMATION: n is a, c, g, or t
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (30)..(32)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: misc_feature
<222> LOCATION: (38)..(40)
<223> OTHER INFORMATION: n is a, c, g, or t

<400> SEQUENCE: 18
gtagcaattg gcaggtccat nnnttnngan nnanngtnnn ccgttgctag gagtctgaat     60

<210> SEQ ID NO 19
<211> LENGTH: 58
<212> TYPE: DNA
<213> ORGANISM: Artificial Sequence
<220> FEATURE:
<223> OTHER INFORMATION: Synthetic oligonucleotide

<400> SEQUENCE: 19
aatgatacgg cgaccaccga gatctacacc aatggagccg acagtaacta cacggcga      58

<210> SEQ ID NO 20
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 20
caagcagaag acggcatacg agatatcgag agcgtagcaa ttggcaggtc cat            53

<210> SEQ ID NO 21
<211> LENGTH: 20
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (6)..(7)
<223> OTHER INFORMATION: n is a, c, g, or t
<220> FEATURE:
<221> NAME/KEY: misc_feature
<222> LOCATION: (10)..(12)
<223> OTHER INFORMATION: n is a, c, g, or t
<220> FEATURE:
<221> NAME/KEY: misc_feature
<222> LOCATION: (14)..(15)
<223> OTHER INFORMATION: n is a, c, g, or t
<220> FEATURE:
<221> NAME/KEY: misc_feature
<222> LOCATION: (18)..(20)
<223> OTHER INFORMATION: n is a, c, g, or t

<400> SEQUENCE: 21
nnnagnntgn nngnnacnnn                                                 20
```

```
<210> SEQ ID NO 22
<211> LENGTH: 20
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (6)..(7)
<223> OTHER INFORMATION: n is a, c, g, or t
<220> FEATURE:
<221> NAME/KEY: misc_feature
<222> LOCATION: (10)..(12)
<223> OTHER INFORMATION: n is a, c, g, or t
<220> FEATURE:
<221> NAME/KEY: misc_feature
<222> LOCATION: (14)..(15)
<223> OTHER INFORMATION: n is a, c, g, or t
<220> FEATURE:
<221> NAME/KEY: misc_feature
<222> LOCATION: (18)..(20)
<223> OTHER INFORMATION: n is a, c, g, or t

<400> SEQUENCE: 22
nnnttnngan nnanngtnnn                                                 20

<210> SEQ ID NO 23
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 23
cttggtcaga cgagtgcatg                                                 20

<210> SEQ ID NO 24
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 24
gagttacgcg gggatacatg                                                 20

<210> SEQ ID NO 25
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 25
tggtacggga acagcacatg                                                 20

<210> SEQ ID NO 26
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 26
```
cgttaagacg tagccccatg                                            20

<210> SEQ ID NO 27
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 27
ctcaccgctc ttgtagcatg                                            20

<210> SEQ ID NO 28
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 28
gaccggcaat ctcttcctgg                                            20

<210> SEQ ID NO 29
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 29
aagacggctg agccatcatg                                            20

<210> SEQ ID NO 30
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 30
ttgtaccttg attcggcatg                                            20

<210> SEQ ID NO 31
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 31
aactctcttt gcgtgccatg                                            20

<210> SEQ ID NO 32
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 32
ccagaatcgt gccttcctgg                                            20

<210> SEQ ID NO 33
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 33
gcaggaatgc aatccgcatg                                              20

<210> SEQ ID NO 34
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 34
caccgtagca tctcaccatg                                              20

<210> SEQ ID NO 35
<211> LENGTH: 56
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (21)..(36)
<223> OTHER INFORMATION: n is a, c, g, or t

<400> SEQUENCE: 35
cgacagtaac tacacggcga nnnnnnnnnn nnnnnncttg gtcagacgag tgcatg       56

<210> SEQ ID NO 36
<211> LENGTH: 56
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (21)..(36)
<223> OTHER INFORMATION: n is a, c, g, or t

<400> SEQUENCE: 36
gtagcaattg gcaggtccat nnnnnnnnnn nnnnnngagt tacgcgggga tacatg       56

<210> SEQ ID NO 37
<211> LENGTH: 56
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (21)..(36)
<223> OTHER INFORMATION: n is a, c, g, or t

<400> SEQUENCE: 37
gtagcaattg gcaggtccat nnnnnnnnnn nnnnnntggt acgggaacag cacatg       56

<210> SEQ ID NO 38
<211> LENGTH: 56
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (21)..(36)
<223> OTHER INFORMATION: n is a, c, g, or t

<400> SEQUENCE: 38
cgacagtaac tacacggcga nnnnnnnnnn nnnnnncgtt aagacgtagc cccatg    56

<210> SEQ ID NO 39
<211> LENGTH: 56
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (21)..(36)
<223> OTHER INFORMATION: n is a, c, g, or t

<400> SEQUENCE: 39
gtagcaattg gcaggtccat nnnnnnnnnn nnnnnnctca ccgctcttgt agcatg    56

<210> SEQ ID NO 40
<211> LENGTH: 56
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (21)..(36)
<223> OTHER INFORMATION: n is a, c, g, or t

<400> SEQUENCE: 40
cgacagtaac tacacggcga nnnnnnnnnn nnnnnngacc ggcaatctct tcctgg    56

<210> SEQ ID NO 41
<211> LENGTH: 56
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (21)..(36)
<223> OTHER INFORMATION: n is a, c, g, or t

<400> SEQUENCE: 41
cgacagtaac tacacggcga nnnnnnnnnn nnnnnnaaga cggctgagcc atcatg    56

<210> SEQ ID NO 42
<211> LENGTH: 56
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (21)..(36)
<223> OTHER INFORMATION: n is a, c, g, or t

<400> SEQUENCE: 42
gtagcaattg gcaggtccat nnnnnnnnnn nnnnnnttgt accttgattc ggcatg    56

<210> SEQ ID NO 43
<211> LENGTH: 56
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (21)..(36)
<223> OTHER INFORMATION: n is a, c, g, or t

```
<400> SEQUENCE: 43
gtagcaattg gcaggtccat nnnnnnnnnn nnnnnnaact ctctttgcgt gccatg        56

<210> SEQ ID NO 44
<211> LENGTH: 56
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (21)..(36)
<223> OTHER INFORMATION: n is a, c, g, or t

<400> SEQUENCE: 44
cgacagtaac tacacggcga nnnnnnnnnn nnnnnnaaga cggctgagcc atcatg        56

<210> SEQ ID NO 45
<211> LENGTH: 56
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (21)..(36)
<223> OTHER INFORMATION: n is a, c, g, or t

<400> SEQUENCE: 45
gtagcaattg gcaggtccat nnnnnnnnnn nnnnnngcag gaatgcaatc cgcatg        56

<210> SEQ ID NO 46
<211> LENGTH: 56
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (21)..(36)
<223> OTHER INFORMATION: n is a, c, g, or t

<400> SEQUENCE: 46
cgacagtaac tacacggcga nnnnnnnnnn nnnnnncacc gtagcatctc accatg        56

<210> SEQ ID NO 47
<211> LENGTH: 58
<212> TYPE: DNA
<213> ORGANISM: Artificial Sequence
<220> FEATURE:
<223> OTHER INFORMATION: Synthetic oligonucleotide

<400> SEQUENCE: 47
aatgatacgg cgaccaccga gatctacacc aatggagccg acagtaacta cacggcga     58

<210> SEQ ID NO 48
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 48
caagcagaag acggcatacg agatatcgag agcgtagcaa ttggcaggtc cat           53

<210> SEQ ID NO 49
```

```
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 49
caatggagcc gacagtaact acacggcga                                    29

<210> SEQ ID NO 50
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 50
atcgagagcg tagcaattgg caggtccat                                    29

<210> SEQ ID NO 51
<211> LENGTH: 58
<212> TYPE: DNA
<213> ORGANISM: Artificial Sequence
<220> FEATURE:
<223> OTHER INFORMATION: Synthetic oligonucleotide

<400> SEQUENCE: 51
aatgatacgg cgaccaccga gatctacact ctttccctac acgacgctct tccgatct    58

<210> SEQ ID NO 52
<211> LENGTH: 57
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<223> OTHER INFORMATION: Phosphorylated 5' end

<400> SEQUENCE: 52
gatcggaaga gcacacgtct gaactccagt cacatctcgt atgccgtctt ctgcttg     57

<210> SEQ ID NO 53
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 53
acactctttc cctacacgac gctcttccga tct                               33

<210> SEQ ID NO 54
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 54
gtgactggag ttcagacgtg tgctcttccg atct                              34

<210> SEQ ID NO 55
<211> LENGTH: 16
<212> TYPE: DNA
<213> ORGANISM: Artificial Sequence
<220> FEATURE:
```

```
<223> OTHER INFORMATION: Synthetic oligonucleotide
<220> FEATURE:
<221> NAME/KEY: misc_feature
<222> LOCATION: (1)..(16)
<223> OTHER INFORMATION: n is a, c, g, or t

<400> SEQUENCE: 55
nnnnnnnnnn nnnnn                                                  16

<210> SEQ ID NO 56
<211> LENGTH: 5
<212> TYPE: DNA
<213> ORGANISM: Artificial Sequence
<220> FEATURE:
<223> OTHER INFORMATION: Synthetic oligonucleotide

<400> SEQUENCE: 56 ggggg                                                              5
```

METHODS FOR RETRIEVAL OF SEQUENCE-VERIFIED DNA CONSTRUCTS

PRIORITY CLAIM

This application claims priority to U.S. Provisional Patent Application No. 61/478,016, filed Apr. 21, 2011, the subject matter of which is hereby incorporated by reference, as if fully set forth herein.

STATEMENT OF GOVERNMENT INTEREST

This invention was made with government support under grants R21 CA160080 and R01 HG006768 awarded by the National Institutes of Health. The Government has certain rights in the invention.

BACKGROUND

De novo gene and genome synthesis is a powerful tool in the field of synthetic biology, having a wide variety of applications, including the design of genetic circuits, the engineering of metabolic pathways, and the study of large gene sets. Approaches for synthesizing genes typically involve pooling short overlapping oligonucleotides and using a polymerase or a ligase-mediated reaction to assemble them into larger constructs. Although the per-base accuracy of the starting oligonucleotides can be higher than 99.5%, only a small fraction of the synthesized products ultimately contain the correct sequence. Screening the products for the correct sequence is currently an expensive and time consuming endeavor.

Current methods (e.g., controlled-pore glass (CPG) methods) for chemical oligonucleotide synthesis are costly and have error rates on the order of 1 in 100 to 1 in 200 bp. These factors are barriers to accurate, high throughput and inexpensive synthetic gene and genome construction (Gibson et al. 2010a; Gibson et al. 2008), as these assembly methods rely on having high quality, sequence-verified oligonucleotide precursors. The generation of these precursors typically involves cloning and Sanger sequencing to identify correct molecules for downstream processing.

With increasing scales of oligonucleotide synthesis scale comes a concomitant need to rapidly screen complex synthetic libraries and then selectively retrieve desired, accurate versions of specific sequences. Recent advances in programmable microarray technology have enabled synthesis of thousands to millions of oligonucleotides on a single chip (LeProust et al. 2010). Additionally, significant effort has recently been directed at exploiting programmable microarrays to inexpensively synthesize genes (LeProust et al. 2010, Tian et al. 2004; Borokov et al. 2010). However, it remains a challenge to scale up these approaches due to the high error rate of microchip-based oligonucleotides and the tendency for mispriming as the complexity of the synthesis pools increases. Gene fragment pools synthesized using microchip-based precursors inevitably contain many inaccurate constructs and the abundance of individual sequences can vary by several orders of magnitude. Consequently, the typical practice for verification and retrieval of accurate sequences, which includes cloning, serial colony picking and Sanger sequencing, remains a significant limiting factor regardless of whether CPG methods or microarrays are used to generate oligonucleotide precursors.

There is a strong need for a robust NGS-based screening and retrieval method that is platform independent and more easily implemented. Thus, it would be desirable to develop a fast and inexpensive method that allows for the selection and amplification of a desired oligonucleotide sequence from a mixed pool of desired and undesired oligonucleotides.

SUMMARY

In some embodiments, methods of recovering a sequence-verified target nucleic acid are provided. In some embodiments, such methods may include tagging each member of a nucleic acid library with a first set of adaptor sequences. In some embodiments, the nucleic acid library may include a population of oligonucleotides, a population of single stranded or double stranded gene fragments, a set of synthetic nucleic acids assembled from oligonucleotides, or a mutagenesis library.

In certain embodiments, the members of the nucleic acid library may be tagged with a second set of adaptor sequences. The first and/or second set of adaptor sequences may comprise a dial-out tag sequence that may be completely degenerative sequence or a partially degenerate sequence. In some embodiments, the first and/or second set of adaptor sequences may comprise SEQ ID NO:13, SEQ ID NO:14, SEQ ID NO:15, SEQ ID NO:16, SEQ ID NO:17, SEQ ID NO:18, SEQ ID NO:21, SEQ ID NO:22, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, and SEQ ID NO:48.

In some embodiments, the methods described herein may further include a step of sequencing the tagged members of the nucleic acid library. In some aspects, the sequencing is performed using a platform selected from cyclic-array methods, nanopore sequencing methods, real-time observation of DNA synthesis, sequencing by electron microscopy, dideoxy termination and electrophoresis, microelectrophoretic methods, sequencing by hybridization, and mass spectroscopy methods.

In some embodiments, the methods described herein may further include recovering one or more sequence-verified target nucleic acids from the tagged and sequenced members of the nucleic acid library using a dial-out selection method. In some aspects, the dial-out selection method may include a hybridization-based capture method, a 2-primer based PCR method, a 1-primer PCR method, a linear amplification method, a multiple displacement amplification method, a rolling circle amplification method, or a ligation-based method. According to some embodiments, the dial-out selection method includes targeting the dial-out tag sequence of the sequence-verified target nucleic acid with a complementary PCR primer; and selectively amplifying the sequence-verified target nucleic acid.

In some embodiments, the methods described herein may further include a subassembly step prior to or during the sequencing or the tagged members of the nucleic acid library.

In another embodiment, methods of recovering a sequence-verified target nucleic acid variant are provided. In some embodiments, such methods may include tagging each member of a mutagenesis library with a first set of adaptor sequences such as those described above; sequencing the tagged members of the mutagenesis library; and recovering the sequence-verified target nucleic acid variant from the tagged and sequenced members of the mutagenesis library using a dial-out selection method described herein. The mutagenesis library may be generated using a method of directed mutagenesis, random mutagenesis, insertional mutagenesis, PCR mutagenesis, or a multiplex programmed mutagenesis according to the embodiments described herein.

In other embodiments, methods of synthesizing a DNA construct are provided. According to the embodiments described herein, such methods may include tagging each member of a nucleic acid library with a set of adaptor sequences; sequencing the tagged members of the nucleic acid library; recovering two or more sequence-verified target nucleic acids from the tagged and sequenced members of the nucleic acid library using a dial-out selection method; and assembling the DNA construct using the two or more sequence-verified target nucleic acids.

DETAILED DESCRIPTION

Figure 1:
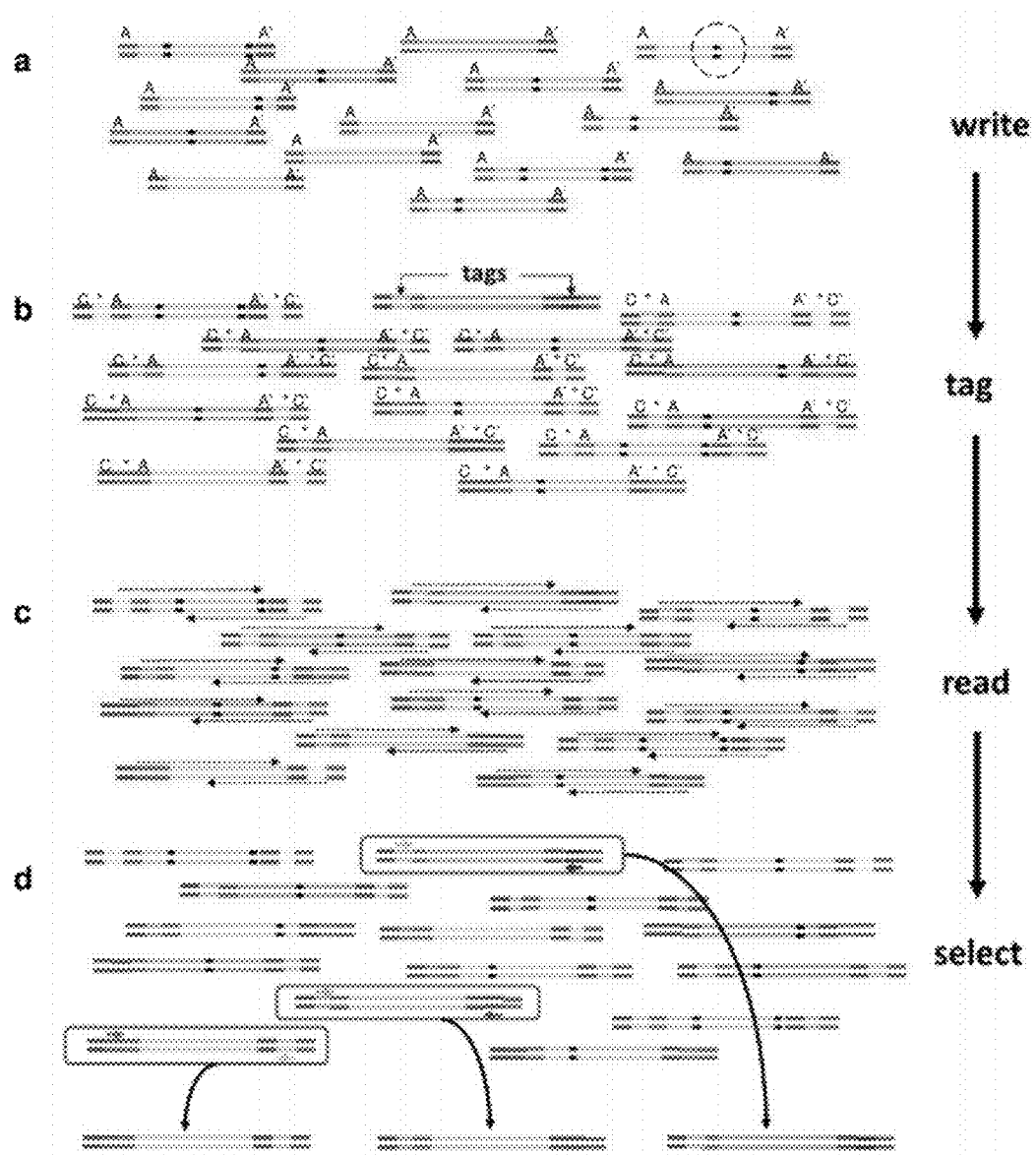
FIG. 1 illustrates a clone-free approach for retrieving a desired oligonucleotide sequence from a complex library. (a) A complex pool that includes 64 different gene fragments, each ~320 bp in length, is synthesized in parallel from microarray-based oligonucleotides. Each oligonucleotide is flanked by common adaptor sequences shown as A and A'. Black marks (e.g., circled) represent errors with respect to the desired sequence. (b) The library is PCR amplified and tagged using primers that contain a common sequence (C and C') and a 15-bp degenerate sequence (*) such that each molecule receives a unique pair of tags. (c) The entire library is then sequenced using next-generation sequencing and tag pairs are associated with specific molecular sequences. (d) PCR primers are designed against tag pairs associated with accurate sequences and they are used to selectively amplify and retrieve them from the complex library.
Figure 2:
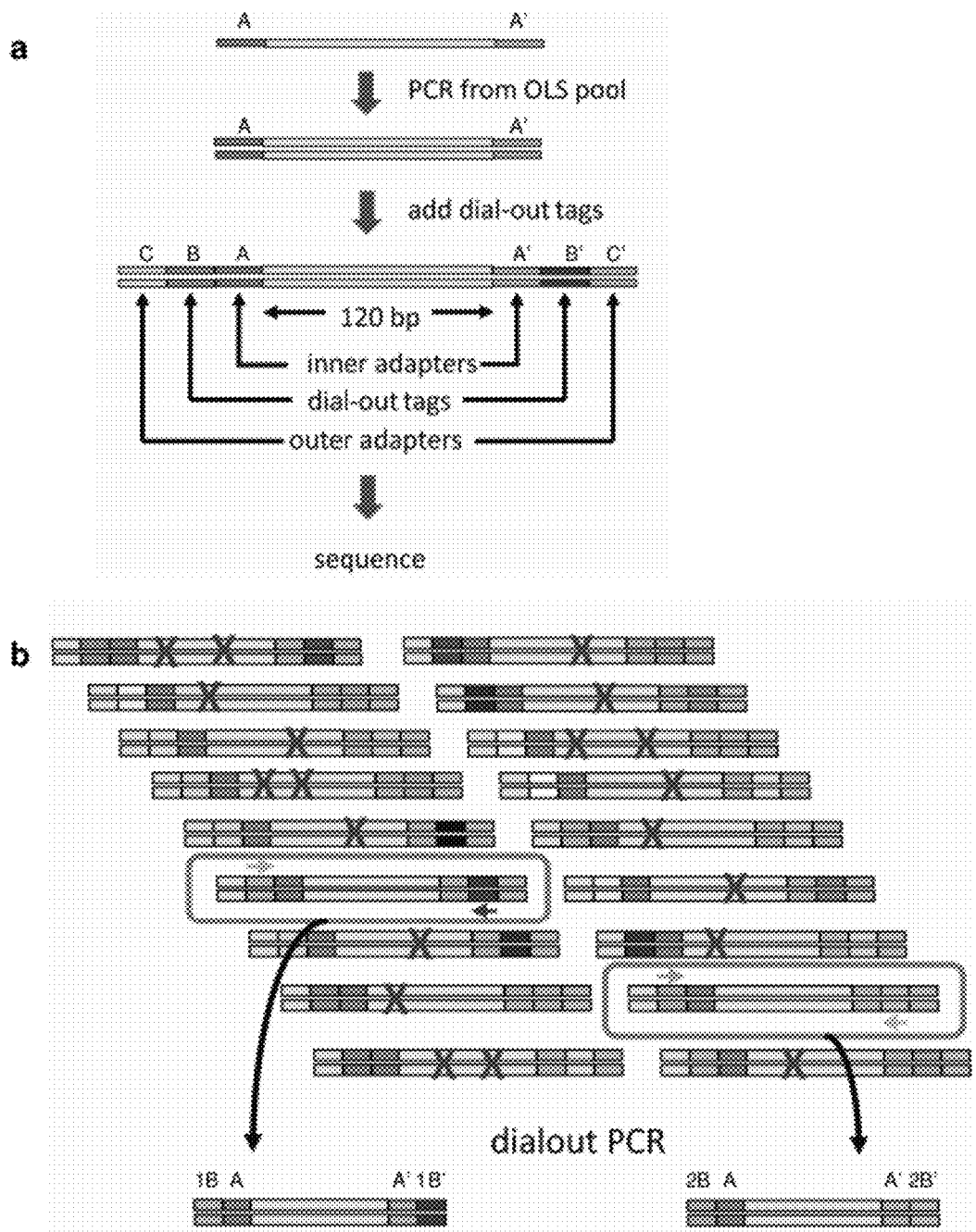
FIG. 2 illustrates dial-out PCR for retrieving accurate sequences from a non-uniform, error-rich library of synthetic DNA molecules. (a) Groups of single-stranded precursors are synthesized and PCR amplified in parallel using common inner adaptors A and A' from column or microarray oligonucleotide precursors. The library is then modified with two unique, flanking "dial-out" tags (B and B') and PCR amplified using a set of common outer adaptors (C and C') before being subjected to massively parallel sequencing. Paired end reads match tags with the internal sequence of the fragment. (b) Dial-out PCR primers are designed against tag pairs associated with accurate sequences and are used to selectively amplify and retrieve them from the original complex library pool. An "X" denotes an error with respect to the accurate target sequence. The retrieved sequences can then processed and assembled into larger accurate constructs.

Provided herein are methods for the selection recovery and amplification of specific molecules of verified sequence (or "sequence-verified target nucleic acid") from a nucleic acid library or pool. According to the embodiments described herein, such methods may be used to generate accurate and lower-cost synthetic genes or genomes of interest (or portions thereof). As referred to herein, a "sequence-verified target nucleic acid" is any suitable DNA molecule or fragment wherein the sequence of said molecule or fragment is known and has been verified using a traditional or new generation sequencing method according to the embodiments described below. According to some embodiments, these methods may include steps of tagging members of an nucleic acid library with an adaptor sequence, sequencing the tagged members of the nucleic acid library and recovering a sequence-verified target nucleic acid using a method of dial-out polymerase chain reaction ("dial-out PCR") (also see FIGS. 1 and 2).

Nucleic Acid Library

The methods described herein may be used with any nucleic acid library or pool. The nucleic acid library may include the one or more desired target oligonucleotide sequences as well as a plurality of undesired or inaccurate oligonucleotide sequences. In some embodiments, members of the library or pool of nucleic acids may include, but is not limited to, a population of oligonucleotides (sometimes referred to herein as an "oligonucleotide pool"); a population of single stranded or double stranded gene fragments, synthetic nucleic acids or constructs assembled from oligonucleotides; a mutagenesis library; or a library of cloned nucleic acid sequences derived from genomic DNA or cDNA.

In certain embodiments, the population of oligonucleotides or gene fragments that make up the nucleic acid library may be derived from genomic DNA, or mRNA. In such embodiments, the nucleic acid library may be generated by one or more methods used in shotgun sequencing including, but not limited to, fragmenting or shearing an isolated DNA sequence to produce a set of DNA fragments or oligonucleotides.

In other embodiments, the mutagenesis library may be generated using a method of directed mutagenesis, random mutagenesis, insertional mutagenesis, PCR mutagenesis, or a multiplex programmed mutagenesis method known in the art. In such embodiments, the methods described herein may be used to recover specific variants of a given gene containing mutations of interest from mutagenesis libraries.

In some embodiments, a known DNA sequence of interest, (e.g., a chromosome, a gene, or a portions thereof) may be used to design and synthesize an nucleic acid library. In certain embodiments, the nucleic acid library may be obtained by synthesizing gene fragments in parallel using conventional polymerase chain assembly methods, CPG methods, or ligation-based methods starting from microarray oligonucleotide precursors. This process results in a mixture of products containing correct (or desired) and incorrect (or undesired) sequences due to errors in the starting material, mispriming, and imperfect enzymes (FIG. 1a). The relative abundance of individual products within the library can also vary over several orders of magnitude due to different efficiencies of assembly.

In some embodiments, the nucleic acid library may be obtained from a commercial source. For example, the nucleic acid library may be an oligonucleotide library synthesis (OLS) pool generated using Agilent's OLS technology or any other suitable technology including, but not limited to, technologies by CustomArray, MycroArray and LC Sciences. Alternatively, the methods described herein may optionally include a step of designing and/or synthesizing gene fragments.

Tagging Members of the Nucleic Acid Library

According to some embodiments, the methods described herein may include tagging, the 3' and/or 5' ends of each member of a nucleic acid library with a set of adaptor sequences. The set of adaptor sequences may include one or more common (or constant) sequences and a unique identification (or "dial-out") tag. In some embodiments, each member is tagged with a set of adaptor sequences on both the 3' and the 5' ends, providing each member with 2 unique dial-out tags. In another amendment, each member is tagged with one set of adaptor sequences on the 3' or the 5' end, providing each member with one unique dial-out tag. In this case, a constant adaptor sequence may be added to the non-tagged end of each member.

In some embodiments, the set of adaptor sequences includes a dial-out tag sequence which is unique to each member of the nucleic acid library. The dial-out tag sequence may also act as a selection sequence (e.g., a PCR priming site) to guide the selection and retrieval (or recovery) of one or more specific target nucleic acid molecules (e.g., sequence-verified target nucleic acids) using a dial-out method such as those described further below. In some embodiments, the dial-out tag sequence comprises the whole selection sequence, whereas in other embodiments, the dial-out tag sequence comprises at least a portion of the selection sequence.

The dial-out tag sequence may be of any suitable length that allows for generating a sufficient number of unique tags sufficient to allow each member of the nucleic acid library to be tagged with a unique dial-out tag sequence on one or both ends. In some embodiments, the dial-out tag sequence is between approximately 5 to 30, 5 to 25, 5 to 20, 5 to 15, 5 to 10, 10 to 30, 10 to 25, 10 to 20, 10 to 15, 15 to 30, 15 to 25, 15 to 20, 20 to 30, 20 to 25, 25 to 30 or more than 30 nucleotides in length. In other embodiments, the dial-out tag sequence is approximately 5, 6, 7, 8, 9, 10, 11, 12, 13, 14, 15, 16, 17, 18, 19, 20, 21, 22, 23, 24, 25, 26, 27, 28, 29, 30 or more than 30 nculeotides in length. In other embodiments, the dial-out tag sequence may be up to and approximately 100 or more nculeotides in length. Regardless of its length, the dial-out tag sequence may include a completely degenerate sequence, a partially degenerate sequence, or a known, non-degenerate sequence.

In certain embodiments, the dial-out tag sequence may be a completely degenerate sequence. For example, a dial-out tag sequence that is 16 nucleotides in length (16-mer) may have a completely degenerate sequence 5'-N NNN NNN NNN NNN NNN-3' (SEQ ID NO:55), wherein each N may be any natural or non-natural nucleotides. A completely degenerate 16-mer gives rise to at least $4 \times 10^9$ different dial out tag sequences, allowing each member of a library comprising $4 \times 10^9$ sequences to be tagged with a unique identifier. Although a 16-mer is used as an example, it is understood that the completely degenerate sequence may be of any suitable length as discussed above.

In other embodiments, the dial-out tag sequence may be a partially degenerate sequence interspersed with constant bases. For example, in one embodiment, a dial-out tag may be 20 nucleotides in length (20-mer) having 15 degenerate nucleotides interspersed with five fixed or constant nucleic acids. In some embodiments, the dial-out tag sequence may be SEQ ID NO:22 or SEQ ID NO:23. In other embodiments, a partially degenerate sequence may include a plurality of constant nucleic acids that are designed to contain a particular CG bias or percentage (e.g., under 40% CG, 40-45% CG, 45-50% CG, 50-55% CG, 55-60% CG, or over 60% CG). Although a 20-mer is used as an example, it is understood that the partially degenerate sequence may be of any suitable length as discussed above. Further, the portions of the partially degenerate sequence that are degenerate or fixed may be determined or designed to be any length or portion thereof, and in any suitable combination.

In other embodiments, the members of a library of nucleic acids may be tagged with a set of known, non-degenerate dial-out tag sequences. The set of known, non-degenerate dial-out tag sequences may be part of a static library of identification tags as described further below. The static library may be designed such that each known dial-out sequence is different for each member.

In some embodiments, the set of adaptor sequences may also include one or more common (or "constant") sequences. The common sequences may be used as, for example, PCR priming sites for amplification of all members of the nucleic acid library, group-specific identification sequences (described further below), and sequences used in an NGS method (e.g., flowcell compatible primers for Illumina sequencing and adaptors for emulsion PCR for 454/Ion Torrent sequencing).

In certain embodiments, the set of adaptor sequences may include an inner common sequence, a dial-out tag sequence and an outer common sequence. The set of adaptor sequences may include, but are not limited to, those shown in Table 8 (SEQ ID NO:13 to SEQ ID NO:18) and Table 18

(SEQ ID NO:35 to SEQ ID NO:48), according to some embodiments. The inner common sequence may be used as a PCR priming site for amplifying all members of a nucleic acid library. Inner common sequences may include, but are not limited to those shown in Table 3 (SEQ ID NO:1 to SEQ ID NO:12) and Table 16 (SEQ ID NO:23 to SEQ ID NO:34), according to some embodiments. As described herein, the dial-out tag sequence may be used as a target after sequencing to selectively amplify one or more accurate or desired target nucleic acid sequences. Dial out tags may include, but are not limited to, SEQ ID NO:22, SEQ ID NO:23, and SEQ ID NO:55, according to some embodiments. The outer common sequence may be used as an additional PCR priming site, or may be used as a group-specific identification sequence. Additional inner and/or outer common sequences may also be included if and when necessary, such as when the library is further divided or combined into different groups or when additional amplification steps are needed.

The adaptor sequences described above may be added to one or both ends (i.e., the 5' end, the 3' end, or both the 3' and 5' ends) of each member (FIG. 1b) using any suitable PCR or ligation method including, but not limited to A-tailing or T-tailing using polymerase extension or any other suitable enzyme; blunt end ligation; using a restriction enzyme to create a single nucleotide overhang; or any other method known in the art, such as circularization with a double stranded n-mer containing a linker and cloning or in vitro ligation methods. In some embodiments, unique dial-out tag sequences are embedded as variable subsequences within PCR primers. PCR conditions are chosen to impose a complexity bottleneck such that each molecule has a high probability of receiving a unique pair of tags.

In another embodiment, a first set of adaptor sequences, ABC, and a second set of adaptor sequences, A'B'C', are used to tag the 3' and the 5' ends of each member of a nucleic acid library (FIG. 2a). In such embodiments, the first set of adaptor sequences includes a first inner common sequence (A), a first unique dial-out tag sequence (B), and a first outer common sequence (C) and the second set of adaptor sequences includes a second inner common sequence (A'), a second dial-out tag sequence (B') and a second outer common sequence (C'). As such, a representative member that has been tagged (i.e., added by ligation or PCR) with the first and second set of adaptor sequences may be represented as follows:

5'-(A B C)-(nucleic acid library member)-(A' B' C')-3'

Further, because each tagged member has 2 unique dial-out tags, a nucleic acid library that has 10 members may be represented as follows:

5'-(C B1 A)-(nucleic acid library member)-(A' B1' C')-3'
5'-(C B2 A)-(nucleic acid library member)-(A' B2' C')-3'
5'-(C B3 A)-(nucleic acid library member)-(A' B3' C')-3'
5'-(C B4 A)-(nucleic acid library member)-(A' B4' C')-3'
5'-(C B5 A)-(nucleic acid library member)-(A' B5' C')-3'
5'-(C B6 A)-(nucleic acid library member)-(A' B6' C')-3'
5'-(C B7 A)-(nucleic acid library member)-(A' B7' C')-3'
5'-(C B8 A)-(nucleic acid library member)-(A' B8' C')-3'
5'-(C B9 A)-(nucleic acid library member)-(A' B9' C')-3'
5'-(C B10 A)-(nucleic acid library member)-(A' B10' C')-3'

Moreover, the outer common sequences, C and C' may include group-specific identification sequences. For example a library of oligonucleotides may be divided into two or more groups based on similar characteristics (e.g., % CG content). In one aspect, a nucleic acid library having 10 members may be divided into two 5-member groups as follows:

5'-(C1 B1 A)-(nucleic acid library member)-(A' B1' C1')-3'
5'-(C1 B2 A)-(nucleic acid library member)-(A' B2' C1')-3'
5'-(C1 B3 A)-(nucleic acid library member)-(A' B3' C1')-3'
5'-(C1 B4 A)-(nucleic acid library member)-(A' B4' C1')-3'
5'-(C1 B5 A)-(nucleic acid library member)-(A' B5' C1')-3'
5'-(C2 B6 A)-(nucleic acid library member)-(A' B6' C2')-3'
5'-(C2 B7 A)-(nucleic acid library member)-(A' B7' C2')-3'
5'-(C2 B8 A)-(nucleic acid library member)-(A' B8' C2')-3'
5'-(C2 B9 A)-(nucleic acid library member)-(A' B9' C2')-3'
5'-(C2 B10 A)-(nucleic acid library member)-(A' B10' C2')-3'

Ligations or PCR that result in library members having 5'-(CBA)-(nucleic acid library member)-(A'B'C')-3' product are then selectively amplified using PCR primers targeted against the dial-out sequences, the outer common sequences, or a combination of both. Appropriate sample preparation and next generation sequencing methods can then be used to accurately identify and correlate the degenerate tag and synthesis product sequences. Based on this information, PCR primers can be designed to target the internal tags of the desired product to selectively amplify just that sequence out of the original nucleic acid library. After PCR, the remaining adaptor sequences can be removed using enzymes that recognize and cleave the inner constant sequences. The nature of this method enables selective amplification of any molecule from the original sample pool or nucleic acid library by designing PCR primers or probes against tags which uniquely specify the desired product(s).

Sequencing Members of the Tagged Nucleic Acid Library

According to some embodiments, the methods for selection, recovery and amplification of one or more desired target oligonucleotide sequences may include sequencing the tagged oligonucleotide members of the nucleic acid library. In some embodiments, the sequencing step may include deeply sequencing the tagged library using any massively parallel sequencing or NGS platform (FIG. 1c). For platforms that do not natively support long (>400 bp) reads, the tags are used to generate effective long reads using subassembly (Hiatt et al. 2010). As most NGS platforms have a non-trivial error rate, the tags are used to generate a consensus sequence for each gene fragment molecule. At this stage, the sequence of the gene fragments and their associated unique tags are known.

Unlike sequence enrichment or other error correction approaches that require cloning (Gibson et al. 2010b), specialized instrumentation (Matzas et al. 2010), enzymatic processing (Bang & Church 2008; Binkowski et al. 2005; Carr et al. 2004; Smith & Modrich 1997), or a specific next-generation sequencing (NGS) platform (Matzas et al. 2010), the methods described herein are compatible with any NGS platform and can be performed by any laboratory capable of doing PCR. In addition, the methods described herein are compatible with many of these error correction methods.

Suitable DNA sequencing technologies that may be used in accordance with the methods described herein may include, but are not limited to, "cyclic-array" methods (e.g., 454 pyrosequencing, Illumina Genome Analyzer, AB SOLiD, and HeliScope), nanopore sequencing methods, real-time observation of DNA synthesis, sequencing by electron microscopy, dideoxy termination and electrophoresis, microelectrophoretic methods, sequencing by hybridization, and mass spectroscopy methods.

To date, there has been only one report of a method using NGS as a preparative tool to verify and retrieve desired sequences (Matzas et al. 2010). The approach involves sequencing a synthetic library on the 454 GS FLX platform and then using a microactuator-controlled micropipette to selectively retrieve clonal beads containing desired sequences for subsequent PCR amplification. While it demonstrates the power of using NGS for screening and retrieving sequences from complex synthetic libraries, it currently has a limited success rate (90%), requires highly specialized instrumentation, and is only compatible with one NGS platform.

Selecting and Retrieving Sequence-Verified Target Nucleic Acids

After sequencing the library of nucleic acids, the sequence of each member of the library is known, and the desired, accurate sequence or sequences are identified and selected for recovery and amplification. Methods for selection, recovery and amplification of one or more desired target nucleic acid sequences include any suitable selection method to exploit the unique dial-out tag sequence to selectively target the desired, accurate sequence or sequences. Such selection methods are referred to herein as "dial-out selection methods." Suitable dial-out selection methods may include, but are not limited to, hybridization-based capture methods, 2-primer based PCR methods directed to members of nucleic acid libraries that are tagged with two sets of adaptor sequences that include two dial-out tag sequences, 1-primer PCR methods directed to members of nucleic acid libraries that are tagged with one set of adaptor sequences having a single dial-out tag sequence, linear amplification, multiple displacement amplification, rolling circle amplification, and ligation-based methods (e.g., selective circularization methods, molecular inversion probes).

According to some embodiments, the dial-out selection method used for selection, recovery and amplification of one or more desired target nucleic acid sequences may be a method of selective amplification referred to herein as "dial-out PCR." A dial-out PCR method is a clone-free and highly parallel method for obtaining sequence-verified nucleic acids (e.g., oligonucleotides or DNA constructs) for simplex or multiplex gene and genome synthesis. Dial-out PCR is a type of 2-primer based PCR method as described below, when each member of a nucleic acid library is tagged with two sets of adaptor sequences resulting in unique dial-out tags on each end. In some embodiments, the dial-out PCR method includes targeting the dial-out tag sequence of the sequence-verified target nucleic acid with a complementary PCR primer and selectively amplifying the sequence-verified target nucleic acid. Any suitable PCR protocol known in the art may be used to amplify the sequence-verified target nucleic acid including, but not limited to those methods described in the Examples below.

As described above, members of a nucleic acid library are modified (or tagged) with a first and/or second set of adaptor sequences, each of which includes a unique, flanking dial-out tag sequence before being subjected to a sequencing method such as massively parallel sequencing. Sets of adaptor sequences and dial-out tags that are suitable for use with dial-out PCR and other selection methods are described above. The dial-out tags act as PCR priming sites or at least a portion of a PCR priming site to enable the retrieval of specific molecules were assembled with accurate sequence.

To demonstrate the dial-out PCR method according to one embodiment (described in Example 1 below), a library of 192 synthetic gene fragments 293-347 bp in length was generated in parallel using microchip oligonucleotide precursors. After sequencing, 58 accurate assemblies were identified, corresponding to 42 unique gene fragments, and used the flanking tags to selectively retrieve them. A subset of the retrieved sequences was then used to build 9 larger accurate constructs ranging in length from 608-878 bp. For retrieval, PCR primers were designed that target the tags of the fragment containing the desired sequence. This "dial-out" PCR produces high purity DNA that can be directly used in downstream gene and genome synthesis applications (FIG. 1d).

Retrieving or recovering the sequence-verified target nucleic acid may include synthesizing PCR primers that are complementary to the tags of the fragment containing accurate sequence (FIG. 2b). A "dial-out" PCR using these primers produces high purity DNA corresponding to the accurate molecule that can be directly used in downstream gene and genome synthesis applications.

Dial-out PCR is a general method or strategy that allows for the use of any next-generation sequencing platform for "massively parallel clone screening" and is thus a compelling in vitro alternative to traditional in vivo cloning, colony picking, and Sanger sequencing. It also allows for the normalization of target sequence abundance after multiplex assembly steps, and has the potential to decrease production costs for high quality, sequence-verified synthetic DNA by two or more orders of magnitude. With careful design, hundreds of 300-600 bp gene fragments may be routinely synthesized in parallel directly from column or microchip oligonucleotides, and then molecules with accurate sequence corresponding to each gene fragment may be recovered using the methods described herein. Furthermore, as it is not NGS platform-specific and does not require any specialized instrumentation, dial-out PCR can be easily and widely adopted by individual researchers. Future development of new sequencing platforms that offer native long reads and short run times, such as the Pacific Biosciences RS, would likely further improve the turnaround time from assembly to retrieval while also enabling the ability to sequence and "dial-out" longer gene fragments. Dial-out PCR or other selection methods described herein may also be used in methods to screen oligonucleotides that haven't been assembled or to recover specific variants of a given gene containing mutations of interest from mutagenesis libraries. Such methods may include a step of assembling a DNA construct using two or more sequence-verified target nucleic acids recovered according to the embodiments described herein. In some aspects, assembly of a DNA construct may be accomplished using any suitable method known in the art including, but not limited to, polymerase cycling (or "chain") assembly (PCA), ligation and homologous recombination. Thus, the embodiments described herein for quick and inexpensive assembly of entire allelic series, genes, chromosomes, or genomes.

Additionally, the studies described in the Examples below demonstrate that dial-out PCR can effectively leverage the power of NGS for the retrieval of accurate gene fragments from a complex mixture of synthetic DNA comprised predominantly of inaccurate sequences. At the multiplexing level described here, the cost of synthesizing a collection of sequence-verified 120 bp gene fragments is $0.03/bp. Retrieval expenses are dominated by the cost of the unique dial-out PCR primers which is currently around $3 for each set or 79% of the estimated cost per assembled gene fragment. (see Table 1 below). The final cost per base is $4.62/160 bp=$0.029/bp for a sequence-verified 160mer. However, this cost is still over an order of magnitude cheaper than the current commercial cost to synthesize accurate, sequence-verified gene fragments at this length. The total time analysis is shown in Table 2.

TABLE 1

Reagent cost breakdown for synthesis and retrieval of accurate 160 bp fragments.

|  | Total cost to process one 160mer pool |
| --- | --- |
| 160mer OLS pool (12,432 oligos) | $2,000 |
| Primers for initial OLS amplification of 6 groups | $ 0.07 |
| Kapa HiFi for six OLS amplifications | $ 4.25 |
| AMPure cleanup | $ 2.88 |
| Kapa HiFi for tagging reaction | $ 4.25 |
| Primers for tagging reaction | $ 0.07 |
| Illumina MiSeq PE151 reagent costs | $ 700 |
| SUBTOTAL PER POOL | $ 2709 |
| SUBTOTAL PER FRAGMENT | $ 0.22 |
|  | Per fragment retrieval costs |
| Dial-out PCR primers | $ 3.65 |
| Kapa HiFi for dial-out PCR | $ 0.75 |
| TOTAL | ($0.22 + $3.65 + $0.75) = $4.62 |

TABLE 2

|  | Time |
| --- | --- |
| Synthesis of 160mer OLS pool | 72 hours |
| PCR of initial groups | 2 hours |
| PCR for tagging reaction | 2 hours |
| Size selection | 2 hours |
| MiSeq PE151 sequencing | 27 hours |
| Data analysis | 1 hour |
| Synthesis of dial-out PCR primers | 24 hours |
| Dial-out PCR | 2 hours |
| TOTAL | 132 hours = 5.5 days |

Moreover, it is believed that the dial-out PCR primer costs could be greatly reduced by using a static library of tags instead of degenerate tags. For example, a standardized adaptor library containing $10^4$ forward tags and $10^4$ reverse tags gives $10^8$ unique possible forward-reverse tag combinations, which is more than sufficient to dial out accurate molecules, even in the context of highly parallel gene assembly and typical oligonucleotide synthesis error rates. It might also be possible to further increase the multiplexing levels and/or the fragment size to further save on reagent costs.

The following examples are intended to illustrate various embodiments of the invention. As such, the specific embodiments discussed are not to be construed as limitations on the scope of the invention. It will be apparent to one skilled in the art that various equivalents, changes, and modifications may be made without departing from the scope of invention, and it is understood that such equivalent embodiments are to be included herein. Further, all references cited in the disclosure are hereby incorporated by reference in their entirety, as if fully set forth herein.

EXAMPLE 1

Systems and Methods for Screening and Recovering Accurate Instances of Synthetically Assembled DNA Constructs Methods 1. Sequence Design Synthetic gene sequences up to 1 kb in length were designed in DNAWorks (Hoover 2002). This produced a nucleic acid library that included a list of six ~160 bp oligonucleotide precursor groups (herein referred to as Groups A-F) required for the PCA-based synthesis of each gene. Adaptor sequences were added to the 5' and 3' ends (Table 3) and sent to Agilent for synthesis using their OLS technology. These adaptor sequences are examples of inner adaptor sequences.

TABLE 3

| Group | 5' adaptor sequence | 3' adaptor sequence |
| --- | --- | --- |
| A | TTATTCGCCCATTTCCCT GG (SEQ ID NO: 1) | /5Phos/TGGTCGAATGGCTGCTG ATC (SEQ ID NO: 2) |
| B | GAGAATGGCTGCTCTCCA TG (SEQ ID NO: 3) | /5Phos/TGGTCGAATGGCTGCTG ATC (SEQ ID NO: 4) |
| C | GGTAGGGTAAAGAGACCT GG (SEQ ID NO: 5) | /5Phos/TGGTCGAATGGCTGCTG ATC (SEQ ID NO: 6) |
| D | GGATACTGGCGGAGTGCA TG (SEQ ID NO: 7) | /SPhos/TGGTCGAATGGCTGCTG ATC (SEQ ID NO: 8) |
| E | ATTTGATGAGTTGCCCCA TG (SEQ ID NO: 9) | /SPhos/TGGTCGAATGGCTGCTG ATC (SEQ ID NO: 10) |
| F | CCGTTGCTAGGAGTCTGA AT (SEQ ID NO: 11) | /SPhos/TGGTCGAATGGCTGCTG ATC (SEQ ID NO: 12) |

2. Multiplex Gene Synthesis

Each set of oligonucleotide precursors were individually amplified, i.e., all 64 precursors in Group A were PCR'ed together, all Group B's together, and so on. For each Group, a 25 μL reaction mixture shown in Table 4 (below) was subjected to the following cycling conditions: (1) 95° C. for 2 minutes; (2) 98° C. for 20 sec; (3) 62° C. for 15 sec; (4) 72° C. for 15 sec; (5) go to (2) 35 times; (6) 72° C. for 5 minutes; and (7) 4° C. forever

TABLE 4

| Mixture Component | Volume |
| --- | --- |
| Kapa2G Robust Hot start Ready-mix | 12.5 all |
| Group-specific forward primer (i.e., specific to Group A, B, C, D, E or F) (10 μM) | 2.5 μL |
| Common reverse primer (10 uM, phosphorylated) | 2.5 μL |
| SYBR Green (x μM) | 0.125 μL |
| Agilent OLS template (x uM) | 0.125 μL |
| Water | To 25 μL |
| TOTAL | 25 μL |

This produced six oligonucleotide pools (A-F), each containing 64 different sequences. Following AMPure cleanup (Agencourt) and elution in 30 uL water, each pool was then treated with lambda exonuclease (exo) to make it single stranded using a mixture (shown in Table 5 below)

subjected to the following conditions: 37° C. for 30 minutes, heat inactivate 75° C. for 10 minutes.

TABLE 5

| Mixture Component | Volume |
|---|---|
| DNA | 30 µL |
| lambda exo | 1 µL |
| lambda exo buffer | 3.45 µL |
| water | 34.55 µL |
| TOTAL | 35 µL |

To remove the common adaptor sequence, a complementary guide oligo was annealed to it by heating the mixture of Table 6 (below) to 95° C. for 5 minutes, then slowly cooling to 4° C. Next, 1 uL DpnII (NEB) was added followed by treatment at 37° C. for 30 minutes and then heat inactivation at 65° C. for 20 minutes.

TABLE 6

| Mixture Component | Volume |
|---|---|
| ssDNA from above (A-F) | 30 µL |
| NEB buffer #3 (New England Biolabs) | 3 µL |
| 10 uM complementary guide | 1 µL |
| TOTAL | 34 µL |

To synthesize libraries of larger fragments, mixtures (shown in Table 7 below) of pairs containing overlapping pools were combined (i.e. A+B, C+D, E+F) and underwent polymerase chain assembly (PCA) using the following cycling conditions: (1) 95° C. for 2 minutes; (2) 98° C. for 20 sec; (3) 62° C. for 15 sec; (4) 72° C. for 15 sec; (5) Go to (2) 35 times; (6) 72° C. 5 minutes; and (7) 4° C. forever. The resulting pools of assembled constructs (AB, CD, EF) included of 64 unique ~280 bp targets flanked by 20 bp adaptor sequences.

TABLE 7

| Mixture Component | Volume |
|---|---|
| Kapa2G Robust Hotstart Readymix | 12.5 µL |
| Group-specific forward primer (10 uM) | 2.5 µL |
| Group-specific reverse primer (10 uM) | 2.5 µL |
| SYBR Green (1X) | 0.125 µL |
| Single-stranded precursors (~1 ng/nL) | 0.125 µL each |
| Water | To 25 µL |
| TOTAL | 25 µL |

3. Tagging the Library

To isolate specific sequences from each of the libraries (or oligonucleotide pools AB, CD, EF) generated above, the members of each group were tagged with adaptor sequences using PCR. As shown in Table 8, the adaptor sequences included a PCR primer site (unbold) dial-out tag sequence (underlined) and a group-specific common sequence (bold).

TABLE 8

Tag containing primers (=adaptor sequences)

Pool   Adaptor Sequence (AB) 5'-CGACAGTAACTACACGGCGA<u>NNNNAGNNTGNNNGNNACNNN</u>TTA TTCGCCCATTTCCCTGG-3' (SEQ ID NO: 13)
5'-GTAGCAATTGGCAGGTCCAT<u>NNNNTTNNGANNNANNGTNNN</u>GAG AATGGCTGCTCTCCATG-3' (SEQ ID NO: 14)

TABLE 8-continued

Tag containing primers (=adaptor sequences)

Pool   Adaptor Sequence (CD) 5'-CGACAGTAACTACACGGCGA<u>NNNNAGNNTGNNNGNNACNNN</u>GG TAGGGTAAAGAGACCTGG-3' (SEQ ID NO: 15)
5'-GTAGCAATTGGCAGGTCCAT<u>NNNNTTNNGANNNANNGTNNN</u>GGA TACTGGCGGAGTGCATG-3' (SEQ ID NO: 16)

(EF) 5'-CGACAGTAACTACACGGCGA<u>NNNNAGNNTGNNNGNNACNNN</u>ATT TGATGAGTTGCCCCATG-3' (SEQ ID NO: 17)
5'-GTAGCAATTGGCAGGTCCAT<u>NNNNTTNNGANNNANNGTNNN</u>CCG TTGCTAGGAGTCTGAAT-3' (SEQ ID NO: 18)

Briefly, each oligonucleotide pool (e.g., AB, CD and EF) was used to prepare a mixture (shown in Table 9 below) and was subjected to the following cycling conditions to generate the tagged oligonucleotides: (1) 95° C. for 2 minutes; (2) 98° C. for 20 sec; (3) 62° C. for 15 sec; (4) 72° C. for 15 sec; (5) go to (2) 35 times; (6) 72° C. 5 minutes; and (7) 4° C. forever. The outer primers were added after 6 cycles to allow for appropriate bottlenecking during the initial extension.

TABLE 9

| Mixture Component | Volume |
|---|---|
| Kapa HiFi Hotstart Readymix | 12.5 µL |
| Tag-containing forward primer (10 nM) | 2 µL |
| Tag-containing reverse primer (10 nM) | 2 µL |
| Outer forward primer (10 µM) | 2.5 µL |
| Outer reverse primer (10 µM) | 2.5 µL |
| Template (1/100 dilution) | 0.5 µL |
| SYBR Green | 0.125 µL |
| Water | To 25 µL |
| TOTAL | 25 µL |

4. Sequencing the Library using NGS

The libraries and the tags were sequenced using a modified subassembly-based approach (Hiatt et al. 2010) on an Illumina GAIIx, 2% spike in, paired 76 run. This required an additional PCR using flowcell compatible primers (Table 10). Reads were mapped back to target oligonucleotide sequences using Burrows-Wheeler Aligner (BWA). Subassembly was performed using a custom python script.

TABLE 10

Primer sequences for flowcell compatibility (tag-tag reads)

AATGATACGGCGACCACCGAGATCTACACCAATGGAGC<u>CGACAGTAA CTACACGGCGA</u> (SEQ ID NO: 19)

CAAGCAGAAGACGGCATACGAGATATCGAGAGC<u>GTAGCAATTGGCAG GTCCAT</u> (SEQ ID NO: 20)

*Unbolded text is the flowcell adaptor sequence
*Bold is the sequencing primer
*<u>Underlined</u> is the common sequence shared with the tagged primers in Table 8

5. Dial-Out PCR

With the tag sequences known for every molecule, 38 molecules (or sequence-verified target nucleic acids) were selected for dial-out PCR based on tag abundance and the similarity of melting temperatures ($T_m$s) between tag pairs. Dial-out primers containing tag sequence and some outer adaptor sequence were ordered from IDT (standard desalting, cost $2 each). Each tagged oligonucleotide library was used to prepare a mixture (shown in Table 11 below) which was subjected to dial-out PCR according to the following cycling conditions to retrieve the desired accurate fragments: (1) 95° C. for 2 minutes; (2) 98° C. for 20 sec; (3) 62° C. for 15 sec; (4) 72° C. for 15 sec; (5) go to (2) 35 times; (6) 72° C. 5 minutes; and (7) 4° C. forever.

TABLE 11

| Mixture Component | Volume |
| --- | --- |
| Kapa HiFi Hotstart Readymix | 12.5 µL |
| Tag-specific Forward primer (10 µM) | 2.5 µL |
| Tag-specific Reverse primer (10 µM) | 2.5 µL |
| Tagged library (0.1 ng) | 0.125 µL |
| SYBR Green (1X) | 0.125 µL |
| Water | To 25 µL |
| TOTAL | 25 µL |

For PCR reactions that gave product of the expected size, the products were AMPured, cloned into a pUC19 vector, and transformed into *E. coli* (Fusion Blue, Clontech). Colonies were picked and templates were prepared for Sanger sequencing using colony PCR as per the manufacturer's instructions (TempliPhi, GE Healthcare). Sanger reads were compared with the corresponding subassembled sequence to identify dial-out errors.

6. Assembly of Larger Constructs

The dial-out PCR products that contained overlapping gene fragments were further processed for polymerase chain assembly (PCA). First, one strand was labeled with 5'-phosphate according to the reaction mixture in Table 12 below.

TABLE 12

| Mixture Component | Volume |
| --- | --- |
| Kapa HiFi Hotstart Readymix | 12.5 µL |
| Common forward primer (10 µM) | 2.5 µL |
| 5'-P common reverse primer (10 Um) | 2.5 µL |
| Dial-out PCR product (0.1 ng) | 0.125 µL |
| SYBR Green (1X) | 0.125 µL |
| Water | To 25 µL |
| TOTAL | 25 µL |

Following AMPure cleanup and elution in 30 µL water, each PCR reaction was then treated with lambda exonuclease (exo) to make it single stranded. Briefly, the reaction mixture in Table 13 below was subjected to cycling conditions of 37° C. for 30 minutes, and heat inactivation at 75° C. for 10 minutes.

TABLE 13

| Mixture Component | Volume |
| --- | --- |
| DNA eluted from AMPure | 30 µL |
| lambda exo | 1 µL |
| lambda exo buffer | 3.45 µL |
| water | 34.55 µL |
| TOTAL | 35 µL |

To remove the common adaptor sequence, a complementary guide oligo was annealed to it by heating the mixture of Table 14 below to 95° C. for 5 minutes, then slowly cooling to 4° C. Next to cut the common adaptor sequences, 1 uL of FatI or StyD4I (NEB) was added followed by treatment at either 55° C. or 37° C. for 30 minutes, followed by heat inactivation at 65° C. for 20 minutes.

TABLE 14

| Mixture Component | Volume |
| --- | --- |
| ssDNA from above | 30 µL |
| NEB buffer #2 (New England Biolabs) | 3 µL |
| 10 uM complementary guide | 1 µL |
| TOTAL | 34 µL |

This produced single stranded DNA that is used to prepare a mixture (Table 15, below) which is ready to be assembled using PCA according to the following conditions: (1) 95° C. for 2 minutes; (2) 98° C. for 20 sec; (3) 62° C. for 15 sec; (4) 72° C. for 50 sec; (5) go to (2) 35 times; (6) 72° C. 5 minutes; and (7) 4° C. forever.

TABLE 15

| Mixture Component | Volume |
| --- | --- |
| Kapa HiFi Hotstart Readymix | 12.5 |
| Forward primer (10 µM) | 2.5 |
| Reverse primer (10 µM) | 2.5 |
| Single stranded precursor 1 (10 gnu) | 0.125 |
| Single stranded precursor 2 (10 ng/up) | 0.125 |
| SYBR Green (1X) | 0.125 |
| Water | To 25 µL |
| TOTAL | 25 |

Reaction products were then AMPured and run on a 6% TBE PAGE gel to assess size. Reactions that gave the correctly sized product were then cloned and Sanger sequenced.

Results and Discussion

To test retrieval using dial-out PCR, 192 synthetic gene fragments ranging in size from 302-343 bp were designed. The sequences were first processed with DNAWorks (Hoover & Lubkowski 2002) to split them into two overlapping ~160 bp segments with matching melting temperatures. The sequences were partitioned into groups of 64 (A-F); each segment was flanked by one of six 20-bp group-specific adaptor sequences and a common 20-bp adaptor sequence. Groups A-F were PCR amplified separately out of a complex 6500 member 200-mer oligo library synthesis (OLS) pool. Following this PCR, the groups were processed using lambda exonuclease to make them single-stranded and DpnII to remove the common adaptor sequence (Matzas et al. 2010). Overlapping groups were then pooled and the contiguous sequences for the 192 gene fragments were PCR assembled in parallel in a single tube.

Figure 3:
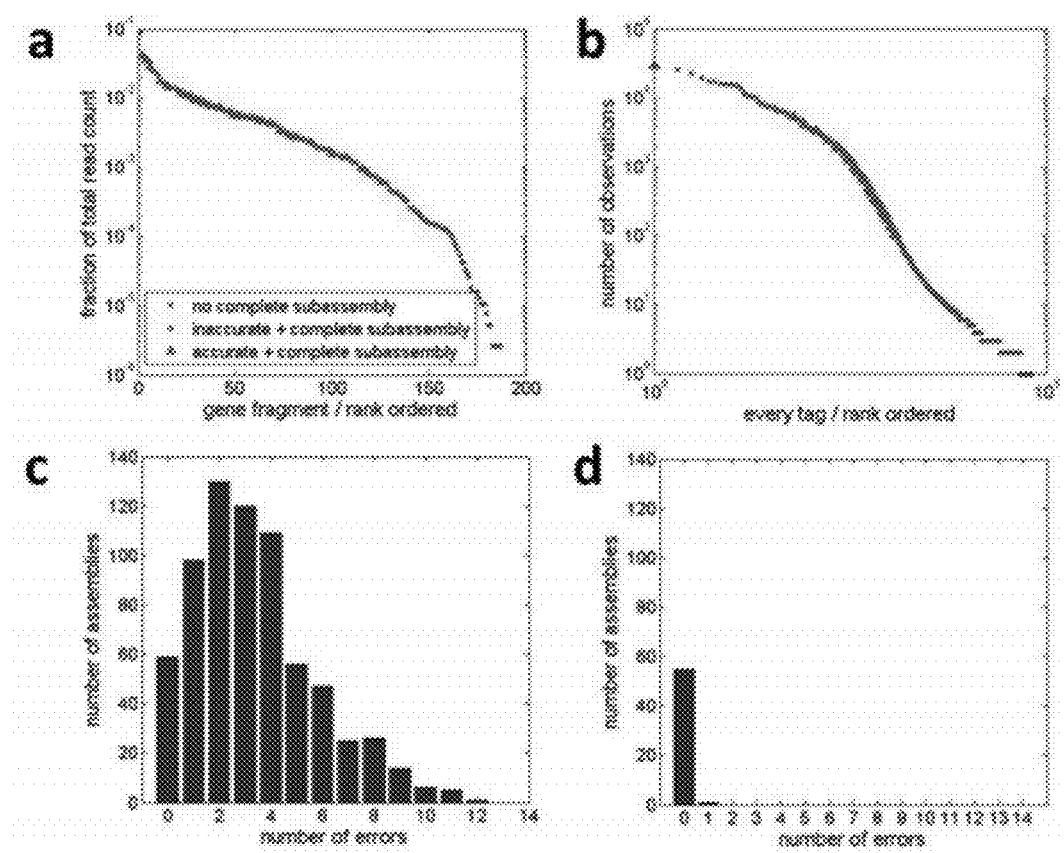
FIG. 3 shows (a) Relative abundance of the 192 synthesized gene fragments based on the total number of mapping reads. Circles are gene fragments that did not have a complete subassembly; Squares represent gene fragments that had at least one complete assembly but none were accurate; and triangles are gene fragments that had at least one subassembly that was complete and accurate. (b) Number of unique tags and the number of times each of those tags were observed in the NGS data. The legend is as in (a). (c) The distribution of errors for the 719 completely subassembled gene fragments in the complex library pool before dial-out PCR. (d) The error distribution for the retrieved 56 gene fragments retrieved after dial-out PCR.
Figure 4:
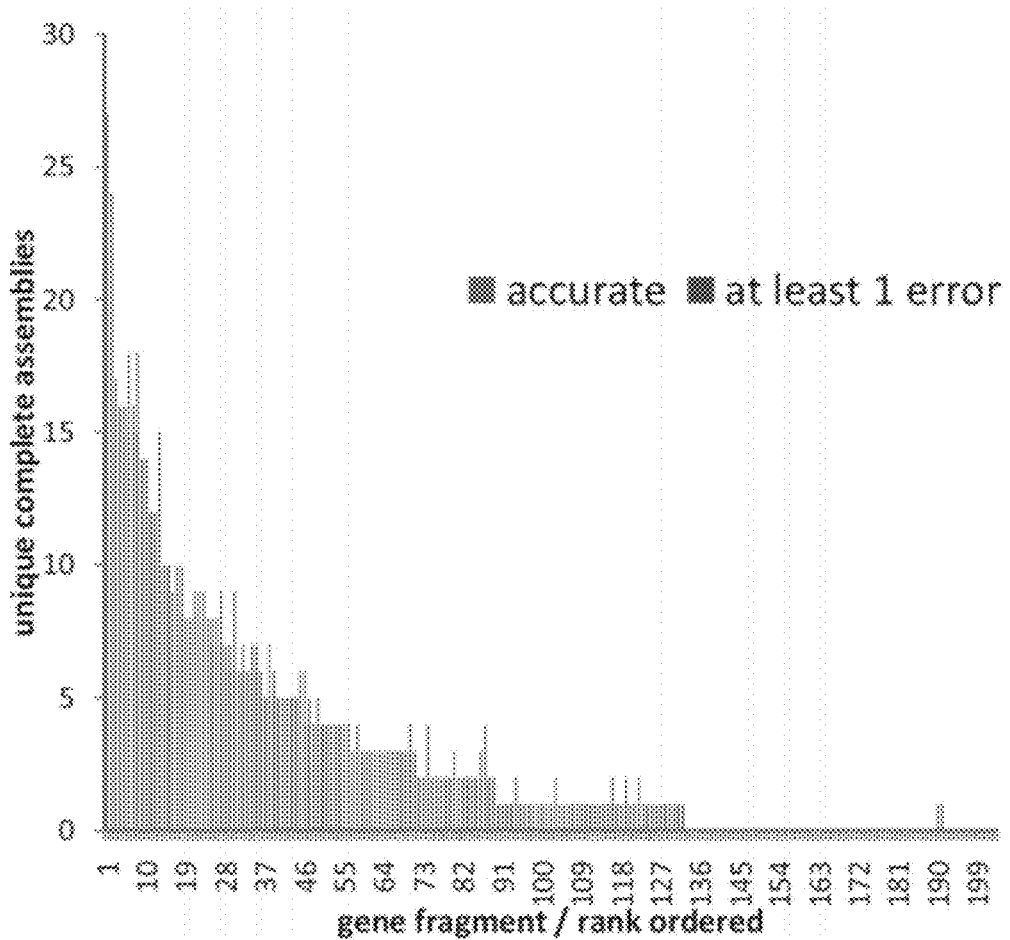
FIG. 4 shows distribution of complete subassemblies over 192 gene fragments according to one embodiment. Dark grey bars indicate subassemblies with at least 1 error; light grey bars represent subassemblies that are accurate. The sequence data was obtained with a 10% spike-in on a PE-76 Illumina GA2 run.

After PCR cleanup, adaptors containing tag sequences were added by PCR using Kapa HiFi, a polymerase engineered for extreme fidelity. The tag sequences consisted of either completely degenerate sequence (N15) or a degenerate sequence interspersed with constant bases, for example, 5'-NNN AGN NTG NNN GNN ACN NN-3' (SEQ ID NO:21) or 5'-NNN TTN NGA NNN ANN GTN NN-3' (SEQ ID NO:22). The sequence of the tagged library was obtained by a 10% spike-in on a single paired-76 lane of an Illumina GAIIx run using tag-directed sequence assembly (Hiatt et al. 2010). Of 1.4M mapping reads, the total number of reads mapping to each of the 192 gene fragments varied over a 4-log range (FIG. 3a) and 1430 different tag pairs were each observed at least 100 times (FIG. 3b). A total of 857,878 (61%) reads contributed to 719 subassemblies that spanned entire gene fragments. Of these, 132/192 gene fragments were covered by at least one complete subassembly, 58 corresponded with complete and accurate sequences, and 42 corresponded with both accurate and unique sequences (FIG. 4). Additional sequencing will likely enable the reconstruction of more complete subassemblies and identify accurate copies of all 192 gene fragments.

Figure 5:
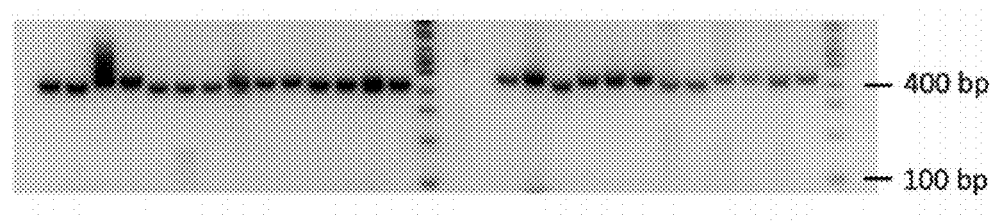
FIG. 5 is a PAGE gel showing 26/56 of the dial-out PCR products.

58 PCR primer sets against the tag pairs corresponding to the accurate subassembled gene fragments were designed. Dial-out PCR with Kapa HiFi gave the correctly-sized product in 56/58 of the reactions (26 of which are shown in FIG. 5). A subset of the retrieved sequences was then used to build 9 larger accurate constructs ranging in length from 608-878 bp using polymerase chain assembly. All 56 of the dial-out PCR products and the 9 larger constructs were cloned in E. coli. Sanger sequencing data showed that all of the dial-out PCRs successfully retrieved the intended gene fragment and that the larger constructs assembled properly. The 65 fragments retrieved or assembled from dial-out PCR spanned a total of 24,414 bp; 64 fragments contained zero errors and one fragment contained a single base error (FIG. 3d). This error likely was introduced post-assembly during the dial-out PCR or during an early round of the TempliPhi plasmid amplification step.

This studies show that dial-out PCR is useful for the retrieval of specific sequences from a complex mixture of oligonucleotides comprised predominantly of inaccurate sequences. At the 64-plex multiplexing levels described here, the cost of synthesizing a ~320 bp fragment is approximately $0.50 ($0.002 per bp). Excluding next-generation sequencing costs, retrieval expenses are dominated by the dial-out PCR primers (~$9 for each set). These combined costs are still over an order of magnitude cheaper than commercial gene synthesis which is currently $0.50/bp. The cost of ordering primers for dial-out PCR could be greatly reduced by moving to a fixed library of tags instead of completely degenerate tags. For example, a standardized adaptor library containing $10^3$ forward tags and $10^3$ reverse tags gives $10^6$ unique possible forward-reverse tag combinations, which is more than sufficient to dial out accurate molecules, even in the context of highly parallel gene assembly and typical oligonucleotide synthesis error rates. It might also be possible to further increase the multiplexing levels to further save on reagent costs.

The method described herein allows one to use any next-generation sequencing (NGS) platform for clone screening and is a compelling alternative to traditional cloning and Sanger sequencing. It allows for the normalization of target sequence abundance after multiplex assembly steps, and has the potential to decrease production costs for high quality, sequence-verified synthetic DNA by two or more orders of magnitude. In one embodiment, hundreds of 300-600 bp gene fragments can routinely be synthesized in parallel directly from microchip oligonucleotides, and then molecules with accurate sequence corresponding to each gene fragment recovered using the method described here. Dial-out PCR can also be used to screen oligonucleotides that haven't been assembled or to recover specific sequences that have mutations of interests from mutagenesis libraries. Desired sequences can then be quickly dialed out by selecting the two appropriate dial-out primers from a standardized tag library. This will help enable the quick and inexpensive assembly of entire allelic series, genes, chromosomes, or genomes. In addition, since it is not NGS platform specific and does not require any specialized instrumentation, it can be easily and widely adopted.

EXAMPLE 2

Tag-Directed Retrieval of Sequence-Verified DNA Constructs for Multiplex Gene Synthesis Methods Oligonucleotide Synthesis and Design Strategy The E. coli K12 substrain DH10B (GenBank CP000948.1) genome sequence was used for the synthesis design. The first 1,246,820 bp of the genome was partitioned into 120 nt individual fragments (12,472 total) and each fragment shared 20 nt of overlapping sequence with its adjacent neighbors to facilitate downstream assembly. No attempt was made to optimize the overlapping regions with regards to length or $T_m$. The fragments were grouped according to their % GC content (<40%, 40-45%, 45-50%, 50-55%, 55-60 and >60% GC) and 20 nt group-specific adaptor sequences were added to the ends to facilitate group specific amplification and retrieval (Table 16). The adaptor sequences contain either a DpnII or StyD4I restriction enzyme recognition site at the 3' end to allow for adaptor removal.

TABLE 16

| Group specific primers for initial amplification | | |
|---|---|---|
| <40% GC-forward (ca_u40_f) | CTTGGTCAGACGAGTGCATG | (SEQ ID NO: 23) |
| <40% GC-reverse (ca_u40_r) | GAGTTACGCGGGGATACATG | (SEQ ID NO: 24) |
| 40-45% GC-forward (ca_40-45_f) | TGGTACGGGAACAGCACATG | (SEQ ID NO: 25) |
| 40-45% GC-reverse (ca_40-45_r) | CGTTAAGACGTAGCCCCATG | (SEQ ID NO: 26) |
| 45-50% GC-forward (ca_45-50_f) | CTCACCGCTCTTGTAGCATG | (SEQ ID NO: 27) |
| 45-50% GC-reverse (ca_45-50_r) | GACCGGCAATCTCTTCCTGG | (SEQ ID NO: 28) |
| 50-55% GC-forward (ca_50-55_f) | AAGACGGCTGAGCCATCATG | (SEQ ID NO: 29) |
| 50-55% GC-reverse (ca_50-55_r) | TTGTACCTTGATTCGGCATG | (SEQ ID NO: 30) |
| 55-60% GC-forward (ca_55-60_f) | AACTCTCTTTGCGTGCCATG | (SEQ ID NO: 31) |
| 55-60% GC-reverse (ca_55-60_r) | CCAGAATCGTGCCTTCCTGG | (SEQ ID NO: 32) |
| >60% GC-forward (ca_o60_f) | GCAGGAATGCAATCCGCATG | (SEQ ID NO: 33) |
| >60% GC-reverse (ca_o60_r) | CACCGTAGCATCTCACCATG | (SEQ ID NO: 34) |

Conventional oligonucleotides used in this work including adaptors, PCR primers, and sequencing primers (see Tables 16, 18, 20 and 24) were obtained from IDT. The OLS pool was synthesized on a programmable microarray at CustomArray using their semiconductor electrochemical process (Maurer et al. 2006).

Amplification and Tagging

Amplification. The raw oligonucleotide pool was initially size selected for ~160 nt molecules to enrich for full length products. The six oligonucleotide pools were then amplified separately using real-time PCR with group specific primers. Briefly, 10 µL of the raw OLS pool from CustomArray (53 ng/µL) was loaded across two lanes on a 6% TBE-UREA gel from Invitrogen. A tight band corresponding to 150-170 nt was excised from the gel and purified. The six group-specific OLS pools were each amplified by preparing a mixture (as shown in Table 17 below) using primer sequences listed in Table 16 above. Each mixture was then subjected to the following cycling conditions on a BioRad MiniOpticon real-time PCR cycler: (1) 95° C. for 2 minutes; (2) 98° C. for 20 sec; (3) 65° C. for 15 sec; (4) 72° C. for 15 sec; (5) go to (2) 35 times; (6) 72° C. 5 minutes; and (7) 4° C. forever.

TABLE 17

| Mixture Component | Volume |
| --- | --- |
| Kapa HiFi Hotstart Readymix | 12.5 µL |
| ca_##_f Forward Primer (10 µM) | 2.5 µL |

TABLE 17-continued

| Mixture Component | Volume |
| --- | --- |
| ca_##_r Reverse Primer (10 µM) | 2.5 µL |
| SYBR Green (100X) | 0.125 µL |
| Size-selected OLS template | ~0.1 ng |
| Water | to 25 µL |
| TOTAL | 25 µL |

Reactions were pulled from the cycler just prior to plateauing, cleaned up using AMPure as per the manufacturer's guidelines (Agencourt), and eluted in 30 µL water. Each pool was then quantified using a Qubit (Invitrogen). The products were purified using AMPure (Agencourt) before undergoing a second PCR to add flanking 16 by degenerate tags and flowcell adaptors as described below.

Tagging. Each group was modified (or "tagged") with adaptors that included a 16 by degenerate tag sequence and an Illumina flowcell adaptor sequence (Table 18). As a result, each member oligonucleotide was tagged with a unique sequence by virtue of the degenerate tag sequence. As shown in Table 18, the adaptor sequences included a flowcell adaptor (unbold) dial-out tag sequence (underlined) and a group-specific common sequence (bold).

TABLE 18

| Tagging primers and flowcell adaptors | |
| --- | --- |
| <40% CG-forward (u40_f_tag) | CGACAGTAACTACACGGCGA<u>NNNNNNNNNNNNNNNN</u>CTTGGTCAGACGAGTGCATG (SEQ ID NO: 35) |
| <40% CG-reverse (u40_r_tag) | GTAGCAATTGGCAGGTCCAT<u>NNNNNNNNNNNNNNNN</u>GAGTTACGCGGGGATACATG (SEQ ID NO: 36) |
| 40-45% CG-forward (40-45_f_tag) | GTAGCAATTGGCAGGTCCAT<u>NNNNNNNNNNNNNNNN</u>TGGTACGGGAACAGCACATG (SEQ ID NO: 37) |
| 40-45% CG-reverse (40-45_r_tag) | CGACAGTAACTACACGGCGA<u>NNNNNNNNNNNNNNNN</u>CGTTAAGACGTAGCCCCATG (SEQ ID NO: 38) |
| 45-50% CG-forward (45-50_f_tag) | GTAGCAATTGGCAGGTCCAT<u>NNNNNNNNNNNNNNNN</u>CTCACCGCTCTTGTAGCATG (SEQ ID NO: 39) |
| 45-50% CG-forward (45-50_r_tag) | CGACAGTAACTACACGGCGA<u>NNNNNNNNNNNNNNNN</u>GACCGGCAATCTCTTCCTGG (SEQ ID NO: 40) |
| 50-55% CG-forward (50-55_f_tag) | CGACAGTAACTACACGGCGA<u>NNNNNNNNNNNNNNNN</u>AAGACGGCTGAGCCATCATG (SEQ ID NO: 41) |
| 50-55% CG-forward (50-55_r_tag) | GTAGCAATTGGCAGGTCCAT<u>NNNNNNNNNNNNNNNN</u>TTGTACCTTGATTCGGCATG (SEQ ID NO: 42) |
| 55-60% CG-forward (55-60_f_tag) | GTAGCAATTGGCAGGTCCAT<u>NNNNNNNNNNNNNNNN</u>AACTCTCTTTGCGTGCCATG (SEQ ID NO: 43) |
| 55-60% CG-forward (55-60_r_tag) | CGACAGTAACTACACGGCGA<u>NNNNNNNNNNNNNNNN</u>AAGACGGCTGAGCCATCATG (SEQ ID NO: 44) |
| >60% CG-forward (o60_f_tag) | GTAGCAATTGGCAGGTCCAT<u>NNNNNNNNNNNNNNNN</u>GCAGGAATGCAATCCGCATG (SEQ ID NO: 45) |
| >60% CG-forward (o60_r_tag) | CGACAGTAACTACACGGCGA<u>NNNNNNNNNNNNNNNN</u>CACCGTAGCATCTCACCATG (SEQ ID NO: 46) |
| ill_tag_amp_f | AATGATACGGCGACCACCGAGATCTACACCAATGGAGCCGACAGTAACTACACGGCGA (SEQ ID NO: 47) |
| ill_tag_amp_r | CAAGCAGAAGACGGCATACGAGATATCGAGAGCGTAGCAATTGGCAGGTCCAT (SEQ ID NO: 48) |

Briefly, each group was amplified by preparing a mixture (as shown in Table 19 below) using Tagging primers and flowcell adaptors listed in Table 18 above. Each mixture was then subjected to the following cycling conditions: (1) 95° C. for 2 minutes; (2) 98° C. for 20 sec; (3) 65° C. for 15 sec; (4) 72° C. for 20 sec; (5) go to (2) 35 times; (6) 72° C. 5 minutes; and (7) 4° C. forever. The outer primers (ill_tag_amp_f and ill_tag_amp_r) were added after 5 cycles to allow for appropriate bottlenecking during the initial extension. Following the PCR, the six reactions were run on a 6% TBE polyacrylamide gel (Invitrogen) and the products were size selected (~310 bp).

TABLE 19

| Mixture Component | Volume |
| --- | --- |
| Kapa HiFi Hotstart Readymix | 12.5 µL |
| Tag 1: 40-45_f_tag (1 nM) | 1 µL |
| Tag 2: 40-45_r_tag (1 nM) | 1 µL |
| Primer 1: ill_tag_amp_f (10 µM) | 2.5 µL |
| Primer 2: ill_tag_amp_r (10 µM) | 2.5 µL |
| Template | ~0.5-4 ng |
| SYBR Green (100X) | 0.125 µL |
| Water | To 25 µL |
| TOTAL | 25 µL |

Sequencing the library on the Illumina MiSeq. The six groups were pooled in proportion to the number of designed sequences within each group. An Illumina MiSeq instrument was operated according to the manufacturer's specifications for paired 151 bp reads. The read 1 and read 2 primers in the MiSeq cartridge were replaced with custom sequencing primers (illum_read1 and illum_read2, Table 20).

TABLE 20

| Sequencing primers | |
| --- | --- |
| illum_read1 | CAATGGAGCCGACAGTAACTACACGGCGA (SEQ ID NO: 49) |
| illum_read2 | ATCGAGAGCGTAGCAATTGGCAGGTCCAT (SEQ ID NO: 50) |

Dial-out analysis pipeline. The paired end 151 bp reads available on the Illumina MiSeq enabled the entire 160 nt oligonucleotide precursor to be sequenced with 110 bp of overlap between reads. The first 16 bp was trimmed from both read 1 and read 2 and this tag sequence was placed in the header for each read. Taken together, each tag pair established membership in a "tag-defined read group" that formed the basis for subsequent analysis.

Reads were mapped to the 12,472 designed target sequences using the Burrows-Wheeler Aligner (BWA). No quality score filtering was done at this stage. Paired reads were piled up based on the tag-defined read group and checked for reference sequence name, CIGAR string, and BWA's optional fields. Within a group, if all of the reads had the same reference sequence and were all accurate according to the CIGAR string and optional fields, the tag pair was flagged as being accurate. Tag pairs that mapped to more than one species were discarded (0.15% of all pairs). Next, 528/12,472 of the designed fragments were randomly selected for retrieval. The majority of these targets had multiple dial-out tag pair candidates to choose from. To maximize retrieval success while keeping the process as simple as possible, the pair that was the most abundant and did not contain a stretch of five or more guanine nucleotides (i.e. GGGGG SEQ ID NO:56) was selected. The $T_m$ of each tag was calculated using the formula I shown below:

$$T_m=81.5+16.6*(\log 10[Na^+])+41*(\% \, GC)-600/(n) \quad \text{(Formula I)}$$

If a tag had a $T_m>=60°$ C., it was selected as a dial-out primer as-is. If a tag had a $T_m<60°$ C., 3 nt were added to the 5' end corresponding to the constant bases in the adaptor sequence (Table 18). This process was repeated until the $T_m$ of the dial-out primer was $>=60°$ C.

Illumina Sequencing

The six groups were pooled in proportion to the number of designed sequences within each group. An Illumina MiSeq instrument was operated according to the manufacturer's specifications for paired 151 bp reads.

Analysis of Tag-Defined Read Groups

The paired end 151 bp reads available on the Illumina MiSeq enabled the entire 160 nt oligonucleotide precursor to be sequenced with 110 bp of overlap between reads. The first 16 bp was trimmed from both read 1 and read 2 and this tag sequence was placed in the header for each read. Taken together, each tag pair established membership in a "tag-defined read group" that formed the basis for subsequent analysis.

Reads were mapped to the 12,472 designed target sequences using the Burrows-Wheeler Aligner (BWA). No quality score filtering was done at this stage. Paired reads were piled up based on the tag-defined read group and checked for reference sequence name, CIGAR string, and BWA's optional fields. Within a group, if all of the reads had the same reference sequence and were all accurate according to the CIGAR string and optional fields, the tag pair was flagged as being accurate. Tag pairs that mapped to more than one species were discarded (0.15% of all pairs).

Dial-Out PCR

528/12,472 of the designed fragments were randomly selected for retrieval. The majority of these targets had multiple unique dial-out tag pair candidates to choose from. To maximize retrieval success while keeping the process as simple as possible, the pair that 1) was the most abundant and 2) did not contain a stretch of five or more guanine nucleotides (i.e. GGGGG; SEQ ID NO:56) was selected. The $T_m$ of each tag was calculated using the formula:

$$T_m=81.5+16.6*(\log 10[Na^+])+41*(\% \, GC)-600/(n)$$

If a tag had a $T_m>=60°$ C., it was selected as a dial-out primer as-is. If a tag had a $T_m<60°$ C., 3 nt were added to the 5' end corresponding to the constant bases in the adaptor sequence (Table 18). This process was repeated until the $T_m$ of the dial-out primer was $>=60°$ C.

Pre-mixed 96 well plates of dial-out primers were ordered from IDT with no additional purification (25 nmol synthesis scale, standard desalting) and accurate sequences were retrieved using dial-out PCR. Briefly, The pre-mixed dial-out primers (5 nmol/well, 12.5 µM in RNAse free water) were used to prepare mixtures shown below in Table 21. The mixtures were then subjected to dial-out PCR according to the following cycling conditions: (1) 95° C. for 2 minutes; (2) 98° C. for 20 sec; (3) 65° C. for 15 sec; (4) 72° C. for 15 sec; (5) go to (2) 35 times; (6) 72° C. 5 minutes; and (7) 4° C. forever.

TABLE 21

| Mixture Component | Volume |
| --- | --- |
| Kapa HiFi Hotstart Readymix | 12.5 µL |
| Dial-out primer mix (12.5 µM each) | 1.0 µL |

TABLE 21-continued

| Mixture Component | Volume |
| --- | --- |
| Tagged synthetic library | ~0.1 ng |
| SYBR Green (1X) | 0.125 µL |
| Water | to 25 µL |
| TOTAL | 25 µL |

Figure 6:
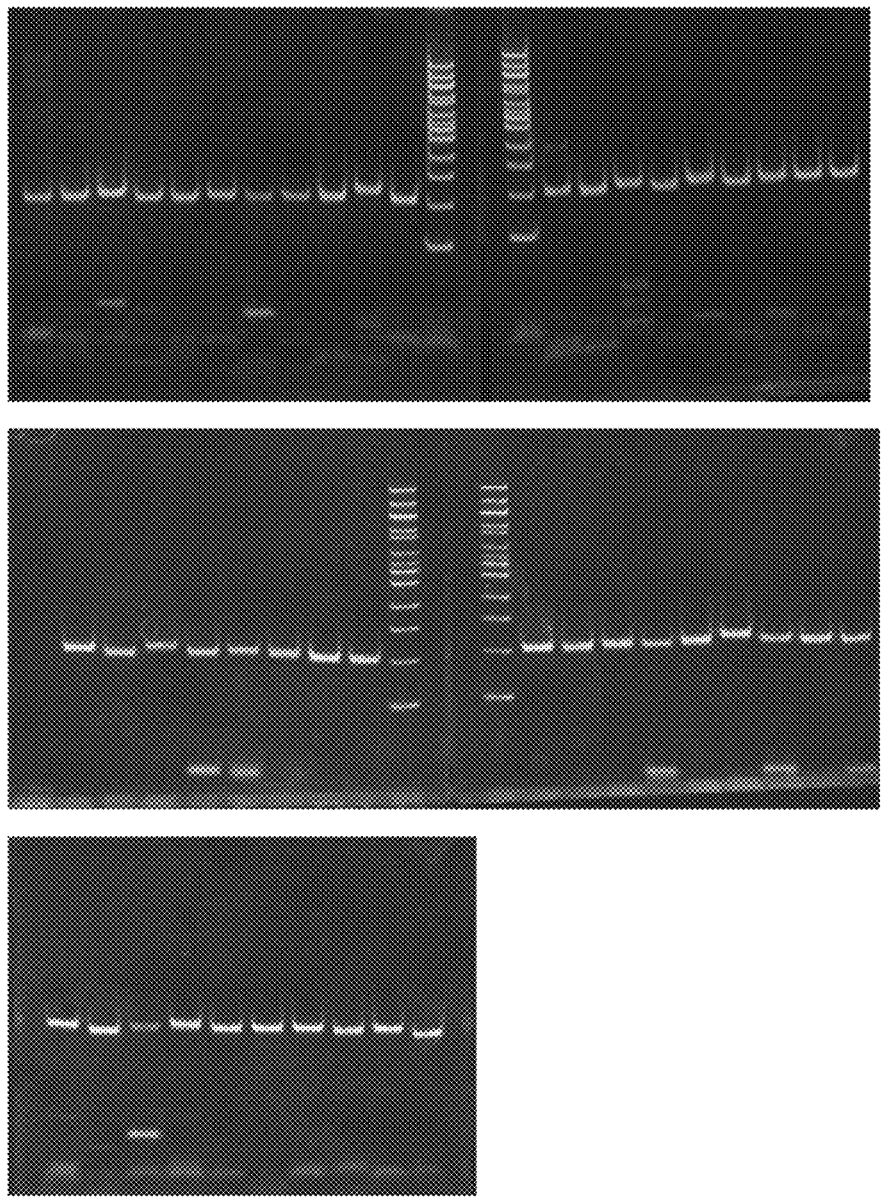
FIG. 6 shows exemplar gel images of 48 of the dial-out PCR products before AMPure purification. The ladder is a 100 bp ladder from NEB; the $2^{nd}$ band corresponds to 200 bp. The expected product size for each lane is (160+16+16+(0-18)=192-210 bp, depending on the number of extra 5' bases that were added to improve the melting temperature ($T_m$) of the dial-out primer.

The PCR products were purified with AMPure (Agencourt) as per the manufacturer's recommendations and eluted in 30 µL water. 48 of the PCR products were run on a 6% TBE gel (Invitrogen) to check the product size (FIG. 6).

Sequence Verification of Dial-Out PCR Products

To verify the accuracy of the retrieved fragments, 5 µL of each clean reaction was taken from each plate and pooled into a single tube (480 µL total volume). The tube was vortexed. Next, the 5' ends of the PCR products were phosphorylated using polynucleotide kinase (PNK, NEB) according to the reaction mixture in Table 22 below. The reaction was held at 37° C. for 45 minutes and then the enzyme was inactivated at 65° C. for 20 minutes. The phosphorylated products were then purified using AMPure and eluted in 44 µL of water.

TABLE 22

| Mixture Component | Volume |
| --- | --- |
| Dialed-out product pool | 34 µL |
| PNK buffer (5X) | 5 µL |
| ATP (100 mM) | 0.5 µL |
| PNK enzyme | 2 µL |
| Water | 8.5 µL |
| TOTAL | 50 µL |

A-tailing. To facilitate direct ligation to sequencing adaptors, the product pool was A-tailed by preparing the mixture shown in Table 23 and subjecting the mixture to a reaction that was held at 70° C. for 20 minutes, followed by AMPure purification and elution in 35 µL of water.

TABLE 23

| Mixture Component | Volume |
| --- | --- |
| Phosphorylated product pool | 44 µL |
| PCR buffer w/ Mg$^{2+}$ (10X, Invitrogen) | 5 µL |
| dATP (100 mM) | 0.5 µL |
| Taq polymerase (5 U/µL, Invitrogen) | 0.5 µL |
| TOTAL | 50 µL |

Flowcell adaptor ligation. Y-tailed adaptors were prepared by mixing 40 µL of 100 µM ill_yad_1 and 40 µL of 100 µM ill_yad_2 (Table 24, below) in 5×SSC, heating to 95° C. for 5 minutes, and cooling to 4° C. at 0.1° C./s. The ligation reaction was performed using the mixture in Table 23 below:

TABLE 25

| Mixture Component | Volume |
| --- | --- |
| A-tailed product pool | 35 µL |
| Y-tailed adaptors (20 µM) | 5 µL |
| Quick Ligation Buffer (2X) | 50 µL |
| Quick Ligase | 10 µL |
| TOTAL | 30 µL |

The ligation reaction proceeded for 15 minutes at room temperature, was AMPured purified, and was then loaded on the Illumina MiSeq as per the manufacturer's recommendations. The read 1 primer used was ill_val_r1 and the read 2 primer was ill_val_r2 (Table 24).

TABLE 24

Adaptors and primers for dial-out product validation

| | |
| --- | --- |
| illum_yad_1 | AATGATACGGCGACCACCGAGATCTACACTCTTTCC CTACACGACGCTCTTCCGATCT (SEQ ID NO: 51) |
| illum_yad_2 | /5Phos/GATCGGAAGAGCACACGTCTGAACTCCA GTCACATCTCGTATGCCGTCTTCTGCTTG (SEQ ID NO: 52) |
| Illum_val_r1 | ACACTCTTTCCCTACACGACGCTCTTCCGATCT (SEQ ID NO: 53) |
| Illum_val_r2 | GTGACTGGAGTTCAGACGTGTGCTCTTCCGATCT (SEQ ID NO: 54) |

Sequence analysis. Paired reads for the dialed-out PCR pool were mapped to the entire 12,472 designed target set using BWA. At this stage, only reads with every base having a quality score>=30 were kept for further analysis. The fraction of perfectly accurate molecules for each dialed-out target was determined by examining the reference sequence name, CIGAR strings, and BWA's optional fields for every read pair.

Results and Discussion

To test retrieval using dial-out PCR, 12,472 synthetic fragments required for the assembly of 1.25 Mb (27%) of the E. coli K12 genome were designed. The fragments were 120 nt in length and tiled in order such that they each shared 20 nt of common sequence with their neighboring fragments. All of the fragments were partitioned into six groups based on GC content (<40%, 40-45%, 45-50%, 50-55%, 55-60%, and >60% GC) to minimize GC bias during PCR. Each group had unique 20 nt adaptor sequences appended to the 5' and 3' ends of its members for a total fragment length of 160 nt. Using these adaptor sequences as primer sites, the six groups were PCR amplified separately out of a complex 12,472 member 160-mer oligonucleotide library synthesis (OLS) pool from CustomArray (Bothell, Wash.). Adaptors containing tag sequences, which were comprised of 16 degenerate bases, 5'-N NNN NNN NNN NNN NNN-3' (SEQ ID NO:55), were then added by PCR using a polymerase engineered for extreme fidelity. The complete sequence of the tagged library was obtained with a single paired-end 151 bp (PE151) run on an Illumina MiSeq.

Figure 7:
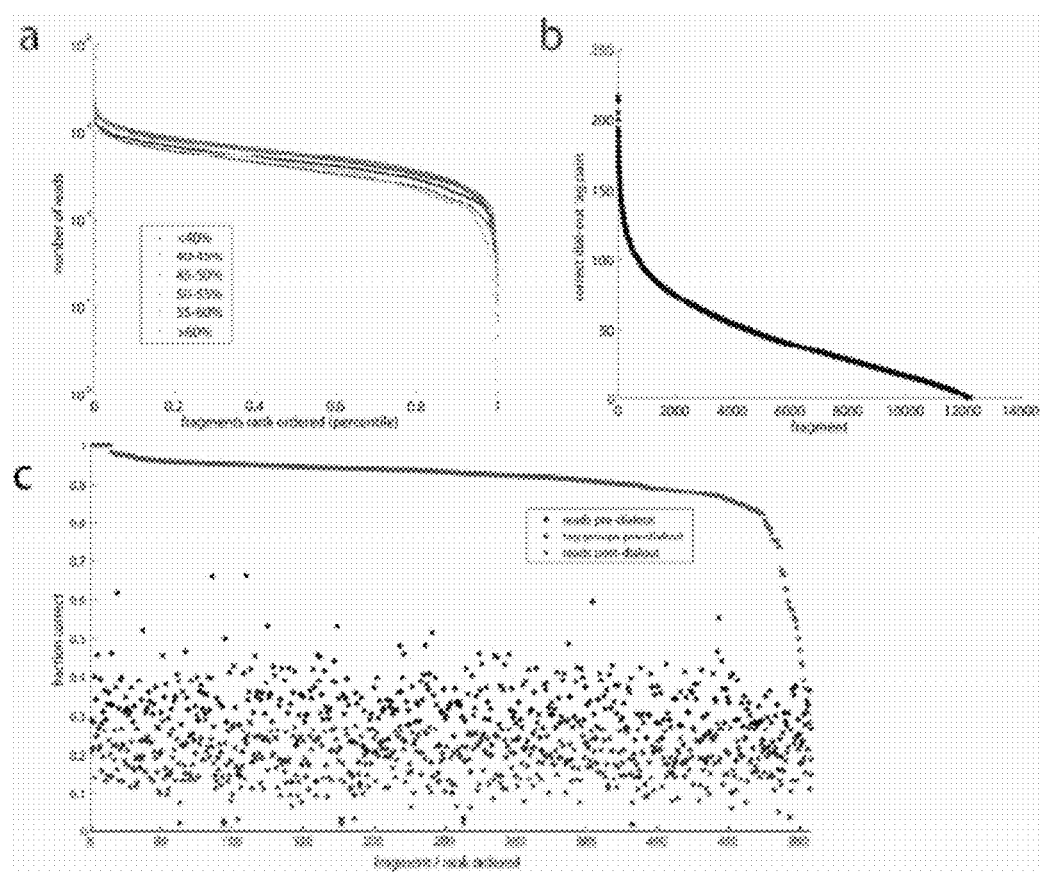
FIG. 7 shows: (a) Uniformity of the six GC groups after initial amplification and tagging. The total number of reads mapping to each of the 12,472 targets is plotted in rank order as the percentile of the total group. 12,221/12,472 (98%) of the designed fragments were observed at least once. (b) The rank ordered distribution of dial-out tag pairs for the 12,206/12,472 fragments that were observed to have at least one accurate sequence. (c) The fraction of correct reads or tag groups for the 528 selected fragments before and after dial-out PCR.
Figure 8:
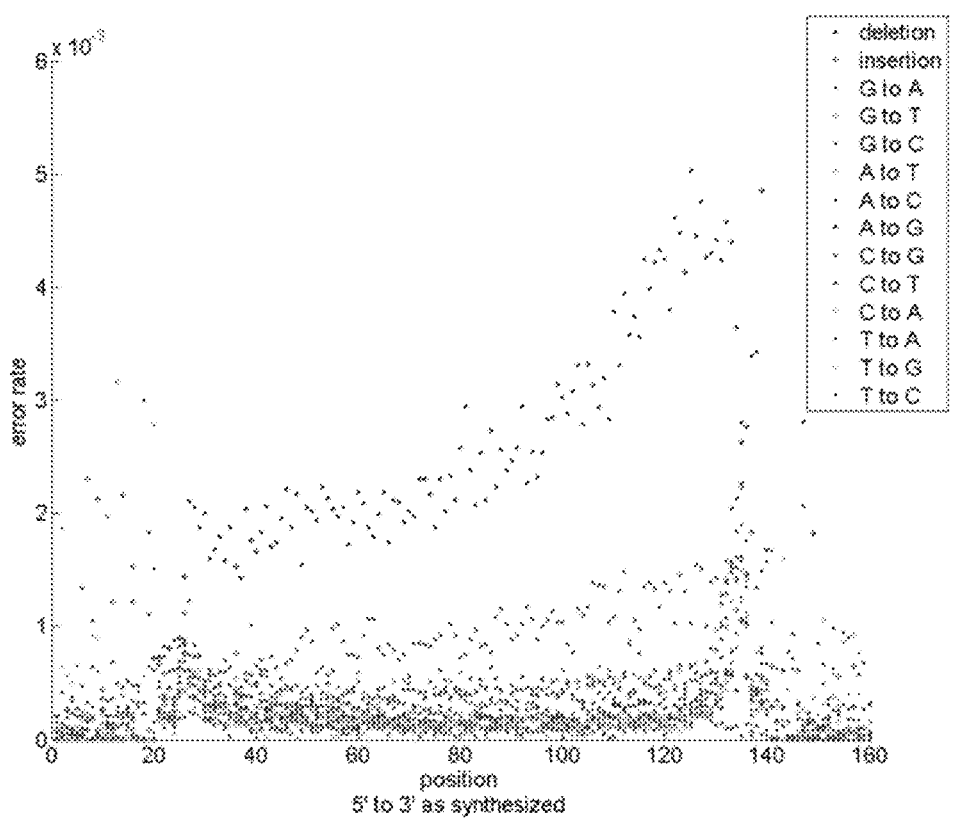
FIG. 8 shows the error profile for the tagged fragment pool. This data was generated using tag group consensus sequences from all fragments and all pools with no quality score filtering. The average error rate between the primer sites (i.e., from position 21 to 140) was ~0.0072/bp or 1/139 bp.
Figure 9:
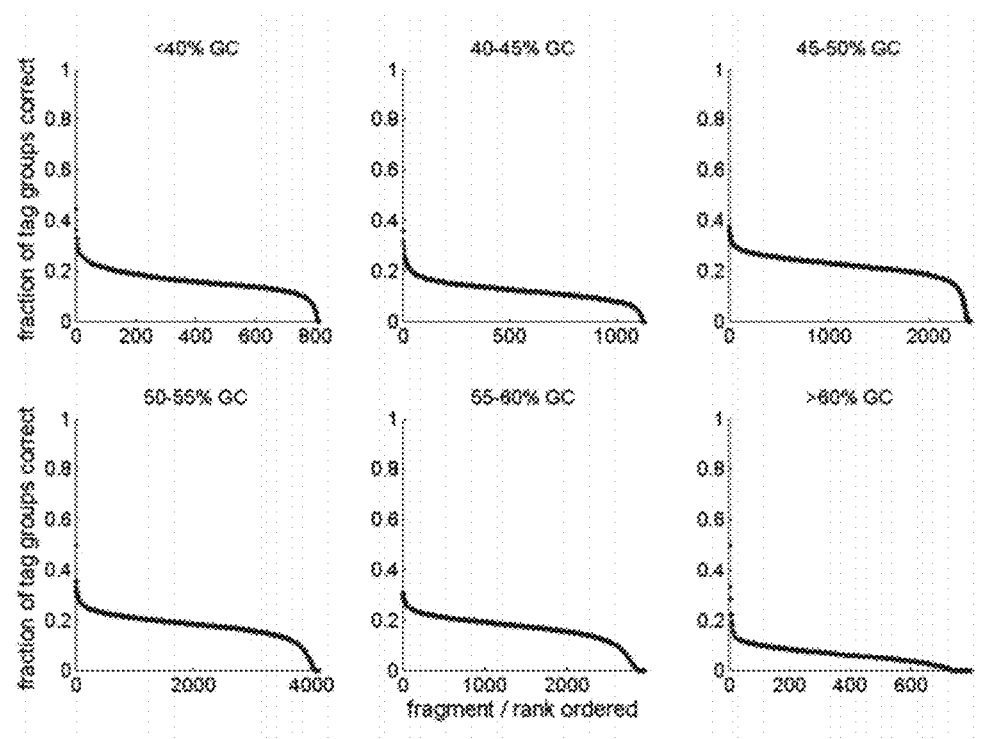
FIG. 9 shows the accuracy of the six GC groups after initial amplification and tagging. For each designed fragment, the fraction of unique tag pairs that were associated with accurate sequence was determined. 12,206/12,472 (97.9%) of the designed fragments had at least one accurate sequence that could be dialed-out.

Of the 5.5 M mapped paired reads, over 90% of the 12,472 fragments had an abundance within an order of magnitude (FIG. 7a). For the five groups with GC<=60%, 11,424/11,424 (100%) of the fragments were observed at least once. In contrast, for the one group with GC>60%, 797/1048 (76%) of the fragments were observed at least once. Collectively, unique dial-out tag pairs corresponding to an accurate sequence for 12,206/12,472 (98%) of the designed fragments were identified (FIG. 7b). On average, each of the 12,206 accurate targets had 45 different unique tag pairs to choose from for retrieval and a total of 41,067 tag pairs were each observed at least 10 times (FIG. 9). The average per-base error rate of the oligonucleotides in the tagged pool was ~1/139 bp (FIG. 8).

528 of the 12,472 designed fragments were randomly selected for dial-out PCR and designed dial-out PCR primer pairs against tags corresponding to accurate molecules. To maximize retrieval success while keeping the process as simple as possible, the tag pair that was the most abundant and did not contain a stretch of five or more guanine nucleotides (i.e. GGGGG; SEQ ID NO:56) was selected. If a tag had a $T_m$>=60° C., it was selected as a dial-out primer as-is; if a tag had a $T_m$<60° C., additional constant bases were added to the 5' end to increase the $T_m$.

Dial-out PCR reactions for 517/528 (97.9%) of the fragments amplified as expected on the real-time PCR instrument and either came up between cycles 25-35 or gave a band of the expected size on a gel. 9/528 (1.7%) of the reactions came up either early or late (before cycle 25 or after cycle 35) and failed to produce a visible band on gel. An examination of the primers selected for these PCRs revealed that many of them appeared likely to form hairpins or homo/heterodimers. 2/528 (0.4%) of the PCRs were completely flat after 45 cycles of PCR and also failed to produce a visible band on a gel; these reactions may have failed due to the absence of the targeted tag pair in the PCR reaction. Aliquots from all 528 PCR reactions were pooled and sequenced on an Illumina MiSeq for validation.

The sequencing data was initially filtered based on quality scores and only kept reads that had a quality score>=25 for every base. For each target, the fraction of correct reads post-dial-out was compared against the fraction of correct reads and tag pairs pre-dial-out (FIG. 7c). It was found that for 472/528 (89%) of the dial-out fragments, >=80% of their reads were perfect with respect to the reference, corresponding to a target enrichment factor of 3 to 27 fold compared to the raw oligonucleotide pool. When more restrictive cutoffs were applied, it was found that 87% of fragments had >=85% of their reads perfect and 73% of fragments had >=90% of their reads perfect. In terms of errors being introduced during dial-out PCR, 30/528 (5.7%) of the dial-out fragments had <80% of their reads correct. These fragments often had a large number of inaccurate reads with a common error present in high abundance. These errors were typically not present in the raw oligonucleotide pool, suggesting that the polymerase introduced them during an early stage of the dial-out PCR. The remaining 26/528 (4.9%) of the dial-out fragments could not be accurately assessed during the validation sequencing run. Of these 26 fragments, 7/528 (1.3%) were observed but did not pass the quality score filter; 8/528 (1.5%) produced a band on a gel but were not observed at all in the sequence data, and 11/528 (2.1%) were not observed in sequence data, did not produced a band on a gel, and had come up early, late, or not at all during the dial-out PCR.

The robustness of dial-out PCR was unexpected, given the lack of strict criteria for primer selection and the potential for cross-hybridization with the complex oligonucleotide pools. Adding an extra step to more rigorously filter out primers that appear problematic would be straightforward to implement and could potentially improve efficiency by 1-2%. Remarkably, seven of the fragments that appeared to fail at the dial-out PCR stage (as evidenced by the lack of a visible band on a gel) still provided enough material to generate high quality sequencing reads. For the 5.7% of fragments that had <80% of their reads correct, accurate retrieval of these sequences might be possible by either repeating the dial-out with the same set of primers or selecting a different set of dial-out primers.

REFERENCES

The references, patents and published patent applications listed below, and all references cited in the specification above are hereby incorporated by reference in their entirety, as if fully set forth herein.

Bang, D. and Church, G. M., *Nat. Meth.* 5 (1), 37 (2008).
Binkowski, B. F., Richmond, K. E., Kaysen, J. et al., *Nucleic Acids Res.* 33 (6), e55 (2005).
Borovkov, A. Y., Loskutov, A. V., Robida, M. D. et al., *Nucleic Acids Res.* 38 (19), e180. (2010)
Carr, P. A., Park, J. S., Lee, Y.-J. et al., *Nucleic Acids Res.* 32 (20), e162 (2004).
Fuhrmann, Markus et al., *Nucleic Acids Research* 33 (6), e58 (2005).
Gibson, D. G., Glass, J. I., Lartigue, C. et al., *Science* 329 (5987), 52. (2010a)
Gibson, D. G., Smith, H. O., Hutchison, C. A. et al., *Nat. Meth.* 7 (11), 901. (2010b)
Gibson, Daniel G., et al., *Science* 319 (5867), 1215 (2008).
Green, R. E., Krause, J., Briggs, A. W. et al., *Science* 328 (5979), 710 (2010).
Hiatt, J. B., Patwardhan, R. P., Turner, E. H. et al., *Nat. Meth.* 7 (2), 119. (2010)
Hoover, D. M. and Lubkowski, J., *Nucleic Acids Res.* 30 (10), e43 (2002).
Kosuri, S., Eroshenko, N., LeProust, E. M. et al., *Nat. Biotech.* 28 (12), 1295. (2010)
LeProust, E. M., Peck, B. J., Spirin, K. et al., *Nucleic Acids Res.* 38 (8), 2522. (2010)
Maurer, K., Cooper, J., Caraballo, M. et al., *PLoS ONE* 1 (1), e34 (2006).
Matzas, M., Stahler, P. F., Kefer, N. et al., *Nat. Biotech.* 28 (12), 1291. (2010)
Smith, J. and Modrich, P., *Proc. Natl. Acad. Sci. USA* 94 (13), 6847 (1997).
Tian, J., Gong, H., Sheng, N. et al., *Nature* 432 (7020), 1050 (2004).

What is claimed is:

1. A method of recovering a sequence-verified target nucleic acid from a sequenced nucleic acid library comprising
  tagging each member of a nucleic acid library with at least one identification tag having a degenerate sequence;
  sequencing the tagged members of the nucleic acid library; and
  selectively recovering only the sequence-verified target nucleic acid from the tagged and sequenced members of the nucleic acid library by targeting the at least one identification tag that is unique to the sequence-verified target nucleic acid using a clone-free dial-out selection method and amplifying the sequence-verified target nucleic acids.

2. The method of claim 1, further comprising tagging each member of the nucleic acid library with a common adaptor sequence.

3. The method of claim 2, wherein the set of adaptor sequences comprises one or more sequences selected from SEQ ID NO:13, SEQ ID NO:14, SEQ ID NO:15, SEQ ID NO:16, SEQ ID NO:17, SEQ ID NO:18, SEQ ID NO:21, SEQ ID NO:22, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, and SEQ ID NO:48.

4. The method of claim 1, wherein the nucleic acid library comprises a population of oligonucleotides, a population of single stranded or double stranded gene fragments, a set of synthetic nucleic acids assembled from oligonucleotides, or a mutagenesis library.

5. The method of claim 1, wherein the sequencing is performed using a massive parallel sequencing platform.

6. The method of claim 1, wherein the dial-out selection method comprises a hybridization-based capture method, a 2-primer based PCR method, a 1-primer PCR method, a linear amplification method, a multiple displacement amplification method, a rolling circle amplification method, or a ligation-based method.

7. The method of claim 1, wherein the dial-out selection method comprises:
  targeting the at least one identification tag that is unique to the sequence-verified target nucleic acid with a complementary PCR primer.

8. The method of claim 1, further comprising a subassembly step prior to or during the sequencing of the tagged members of the nucleic acid library.

9. A method of recovering a sequence-verified target nucleic acid variant comprising:
  tagging each member of a mutagenesis library with at least one identification tag having a degenerate sequence;
  sequencing the tagged members of the mutagenesis library; and
  selectively recovering only the sequence-verified target nucleic acid variant from the tagged and sequenced members of the mutagenesis library by targeting the at least one identification tag that is unique to the sequence-verified target nucleic acid variant using a clone-free dial-out selection method and amplifying the sequence-verified target nucleic acids.

10. The method of claim 9, wherein the mutagenesis library is generated using a method of directed mutagenesis, random mutagenesis, insertional mutagenesis, PCR mutagenesis, or a multiplex programmed mutagenesis.

11. A method of synthesizing a DNA construct comprising:
  tagging each member of a nucleic acid library with at least one identification tag having a degenerate sequence;
  sequencing the tagged members of the nucleic acid library; and
  selectively recovering only two or more sequence-verified target nucleic acids from the tagged and sequenced members of the nucleic acid library by targeting the at least one identification tag that is unique to the two or more sequence-verified target nucleic acids using a clone-free dial-out selection method and amplifying the two or more sequence-verified target nucleic acids; and
  assembling the DNA construct using the two or more sequence-verified target nucleic acids.

12. The method of claim 11, further comprising tagging each member of the nucleic acid library with a common adaptor sequence.

13. The method of claim 12, wherein the set of adaptor sequences comprises one or more sequences selected from SEQ ID NO:13, SEQ ID NO:14, SEQ ID NO:15, SEQ ID NO:16, SEQ ID NO:17, SEQ ID NO:18, SEQ ID NO:21, SEQ ID NO:22, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, and SEQ ID NO:48.

14. The method of claim 11, wherein the nucleic acid library comprises a population of oligonucleotides, a population of single stranded or double stranded gene fragments, a set of synthetic nucleic acids assembled from oligonucleotides, or a mutagenesis library.

15. The method of claim 11, wherein the sequencing is performed using a massive parallel sequencing platform.

16. The method of claim 11, wherein the dial-out selection method comprises:
   targeting the identification tag sequences of the two or more sequence-verified target nucleic acid with a set of complementary PCR primers.

* * * * *